US009044002B2

(12) United States Patent
Hirayama et al.

(10) Patent No.: US 9,044,002 B2
(45) **Date of Patent: *Jun. 2, 2015**

(54) METHOD OF CONTROLLING HARMFUL ARTHROPOD, COMPOSITION, AND ELECTROSTATIC SPRAY DEVICE

(75) Inventors: Takahisa Hirayama, Tokyo (JP); Timothy C Hadingham, Wallingford (GB)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 322 days.

This patent is subject to a terminal disclaimer.

(21) Appl. No.: 13/347,582

(22) Filed: Jan. 10, 2012

(65) Prior Publication Data

US 2012/0178807 A1 Jul. 12, 2012

(30) Foreign Application Priority Data

Jan. 12, 2011 (JP) ................................ 2011-004037
Jan. 21, 2011 (JP) ................................ 2011-011398
Jan. 26, 2011 (JP) ................................ 2011-014408
Jan. 26, 2011 (JP) ................................ 2011-014409
Jan. 26, 2011 (JP) ................................ 2011-014410
Jan. 26, 2011 (JP) ................................ 2011-014411

(51) Int. Cl.

| | |
|---|---|
| ***A01N 53/06*** | (2006.01) |
| ***B05B 5/00*** | (2006.01) |
| ***C07C 69/743*** | (2006.01) |
| ***A01N 53/10*** | (2006.01) |
| ***A01N 53/08*** | (2006.01) |
| ***A01M 1/20*** | (2006.01) |
| ***B05B 5/025*** | (2006.01) |
| ***A01N 53/00*** | (2006.01) |
| *A01P 7/00* | (2006.01) |

(52) U.S. Cl.

CPC .............. *A01M 1/205* (2013.01); *B05B 5/0255* (2013.01); *A01N 53/00* (2013.01)

(58) Field of Classification Search

USPC ............................ 514/531; 560/124; 239/690
See application file for complete search history.

(56) References Cited

U.S. PATENT DOCUMENTS

| | | | |
|---|---|---|---|
| 3,835,176 | A | 9/1974 | Matsuo et al. |
| 3,934,023 | A | 1/1976 | Okuno et al. |
| 4,316,914 | A | 2/1982 | Coffee et al. |
| 4,415,561 | A | 11/1983 | Behrenz et al. |
| RE31,927 | E | 6/1985 | Coffee et al. |
| 4,889,872 | A | 12/1989 | Naumann et al. |
| 6,296,865 | B1 | 10/2001 | Dujardin et al. |
| 6,679,441 | B1 | 1/2004 | Borra et al. |
| 6,908,945 | B2 | 6/2005 | Mori |
| 2003/0195119 | A1 | 10/2003 | Mori |
| 2004/0138475 | A1 | 7/2004 | Hao et al. |
| 2004/0251326 | A1 | 12/2004 | Pirrie |
| 2004/0258764 | A1 | 12/2004 | Murphy et al. |
| 2004/0261194 | A1 | 12/2004 | Price et al. |
| 2005/0000031 | A1 | 1/2005 | Price et al. |
| 2007/0194156 | A1 * | 8/2007 | Pirrie ............................ 239/690 |
| 2008/0265067 | A1 | 10/2008 | Waterman et al. |
| 2009/0270349 | A1 | 10/2009 | Murphy et al. |
| 2009/0326064 | A1 | 12/2009 | Nakamura et al. |
| 2010/0048700 | A1 | 2/2010 | Davies et al. |
| 2013/0022636 | A1 | 1/2013 | Murphy et al. |

FOREIGN PATENT DOCUMENTS

| | | | |
|---|---|---|---|
| AU | B-52829/86 | | 7/1986 |
| AU | 2010236005 | A1 | 5/2011 |
| AU | 2010236006 | A1 | 5/2011 |
| CN | 1067585 | A | 1/1993 |
| CN | 1211162 | A | 3/1999 |
| CN | 1509320 | A | 6/2004 |
| CN | 1249023 | C | 4/2005 |
| CN | 1248784 | C | 4/2006 |
| CN | 1805684 | A | 7/2006 |
| CN | 1813048 | A | 8/2006 |
| CN | 1836512 | A | 9/2006 |
| CN | 101494984 | A | 7/2009 |
| CN | 101792392 | A | 8/2010 |
| EP | 0 003 251 | A1 | 8/1979 |
| EP | 0 629 3 | A1 | 1/1980 |
| EP | 0 019 359 | A1 | 11/1980 |
| EP | 0 019 384 | A1 | 11/1980 |
| EP | 0 669 46 | A1 | 12/1982 |
| EP | 0 009 359 | B1 | 5/1983 |
| EP | 0 224 352 | A1 | 6/1987 |
| EP | 0 320 908 | A1 | 6/1989 |
| EP | 0 520 547 | A2 | 12/1992 |

(Continued)

OTHER PUBLICATIONS

Report on State of the Art & Written Opinion—Spanish Application on No. 201230024 dated Oct. 29, 2012.
Search Report in GB Appln No. 1200328.1 dated May 3, 2012.
Restriction Requirement issued in U.S. Appl. No. 13/814,429 dated Dec. 5, 2014.
Chinese Office Action received in Chinese Application No. 201180037639.1 dated Mar. 26, 2014.
Database WPI Week 200709 Thomson Scientific, London, GB; AN 2007-084504 XP002667600, & CN 1 836 512 A (Honghe Senju Biological Co., Ltd.) Sep. 27, 2006 Abstract.
International Search Report PCT/JP2011/068212 dated Dec. 13, 2011.
International Search Report PCT/JP2011/070673 dated Jan. 2, 2012.
Chinese Office Action received in Chinese Application No. 201180042790.4 dated Nov. 8, 2013.

(Continued)

*Primary Examiner* — Sreeni Padmanabhan
*Assistant Examiner* — Jason A Deck
(74) *Attorney, Agent, or Firm* — Foley & Lardner LLP

(57) ABSTRACT

A method of the present invention, for controlling a harmful arthropod employs an ester compound which has a specific structure. Accordingly, with the method of the present invention, it is possible to control a wide variety of harmful arthropods effectively, without carrying out any heating process (e.g., a smoking process) for spraying the composition or any pressure process (e.g., a gas-pressure process or a mechanical pressure process) for spraying the compositions.

2 Claims, 1 Drawing Sheet

(56) References Cited

FOREIGN PATENT DOCUMENTS

| | | | | |
|---|---|---|---|---|
| EP | 0 523 960 | A1 | | 1/1993 |
| EP | 0 926 129 | A1 | | 6/1999 |
| EP | 0 962 139 | A1 | | 12/1999 |
| EP | 1 004 569 81 | | | 3/2003 |
| EP | 1 399 265 | B1 | | 12/2004 |
| GB | 2 487 290 | A | | 7/2012 |
| JP | 49-054529 | | | 5/1974 |
| JP | 51-005450 | | | 2/1976 |
| JP | 53-091125 | | | 8/1978 |
| JP | 63-203649 | | | 8/1988 |
| JP | 64-011607 | B2 | | 2/1989 |
| JP | 10-298016 | A | | 11/1998 |
| JP | 11-222463 | | | 8/1999 |
| JP | 2000-281515 | A | | 10/2000 |
| JP | 2007-097738 | | | 4/2007 |
| JP | 2008-508150 | | | 3/2008 |
| JP | 2011-116738 | | | 6/2011 |
| WO | WO-00/66206 | | | 11/2000 |
| WO | WO-03/000431 | A1 | | 1/2003 |
| WO | WO-03/018732 | A1 | | 3/2003 |
| WO | WO-2004/089552 | A2 | | 10/2004 |
| WO | WO-2006/010944 | A1 | | 2/2006 |
| WO | WO-2007/040157 | A1 | | 4/2007 |
| WO | WO 2007/083164 | A2 | | 7/2007 |
| WO | WO 2009031692 | A2 | * | 3/2009 |
| WO | WO-2011/062299 | A1 | | 5/2011 |
| WO | WO-2012/033214 | A1 | | 3/2012 |
| WO | WO-2012/096117 | A1 | | 7/2012 |

OTHER PUBLICATIONS

Taylor, G. "Disintegration of water drops in an electric field", Disintegration of Water Drops, Feb. 21, 1964, pp. 383-397.

Chinese Office Action dated May 21, 2014 issued in Application No. 201210004341.7.

Lindser F Gaunt et al., "Electrostatic deposition of charged insecticide sprays on electrically isolated insects", Journal of Electrostatics, 2003, vol. 57 (2003), pp. 35-47.

Office Action issued in Japanese Application No. 2011-011398 dated Oct. 14, 2014.

Office Action issued in Japanese Application No. 2011-014408 dated Oct. 14, 2014.

Office Action issued in Japanese Application No. 2011-014409 dated Oct. 14, 2014.

Office Action issued in Japanese Application No. 2011-014410 dated Oct. 14, 2014.

Office Action issued in Japanese Application No. 2011-190937 dated Oct. 14, 2014.

Suguru Yamane, Heisei 22 nendo nousei kadai kaiketsu kensyu "Yasai no shoryoku teikosuto saibai gijutsu" shiryo (Material for fiscal 2010 training in solving issues of agricultural administration "Techniques of Labor-saving and low-cost vegetable cultivation"), Seiden boujo gijutsu no gaiyou (Outline of electrostatic pest control techniques), Nov. 16, 2010, pp. 1 -6.

Office Action issued in Chinese Appication No. 201210004341.7 dated Nov. 24, 2014.

Office Action issued in Chinese Application No. 201180037639.1 dated Oct. 23, 2014.

Restriction Requirement issued in U.S. Appl. No. 13/821,292 dated Nov. 24, 2014.

Office Action issued in Chinese Patent Application No. 201180042790.4 dated Jul. 28, 2014.

Office Action dated Mar. 31, 2014 issued in Malaysian Application No. PI 2011006356.

"221 cyphenothrin [(1R)-trans-isomers]" in "A World Compendium The Pesticide Manual, Fifteenth Edition" (Jan. 1, 2009), British Crop protection Council (BCPC), XP055157398, pp. 286-287.

"586 metofluthrin" in "A World Compendium—The Pesticide Manual, Fifteenth Edition" (Jan. 1, 2009), British Crop protection Council (BCPC), XP055157389, pp. 778-779.

669 phenothrin [(1R)-trans-isomer] in "A World Compendium The Pesticide Manual, Fifteenth Edition" (Jan. 1, 2009), British Crop protection Council (BCPC), XP055157396, pp. 885-886.

"695 prallethrin" in "A World Compendium The Pesticide Manual, Fifteenth Edition" (Jan. 1, 2009), British Crop protection Council (BCPC), XP055157393, pp. 923-924.

"863 transfluthrin" in A World Compendium The Pesticide Manual, Fifteenth Edition (Jan. 1, 2009), British Crop protection Council (BCPC), XP55157394, pp. 1143-1144.

Search Report issued in French Patent Application No. 1250236 dated Dec. 18, 2014.

Tang G et al., "Natural pyrethrin super low-vol. spraying agent and static spraying insect-guarding method", WPI/Thomson, vol. 2007, No. 9, XP002667600, Sep. 27, 2006.

Masao Hagihara, "Journal of the Japan Society of Colour Materials", 1964, vol. 37, No. 6, p. 216-224.

Office Action issued in Japanese Patent Application No. 2011-014408 dated Jan. 20, 2015.

Office Action issued in Japanese Patent Application No. 2011-014409 dated Jan. 13, 2015.

Office Action issued in Japanese Patent Application No. 2011-014410 dated Jan. 20, 2015.

Office Action issued in Japanese Patent Application No. 2011-190937 date Jan. 20, 2015.

Office Action dated Feb. 12, 2015 issued in U.S. Appl. No. 13/821,292 which is co-pending application of present application.

Office Action dated Feb. 13, 2015 issued in U.S. Appl. No. 13/814,429 which is co-pending application of present application.

* cited by examiner

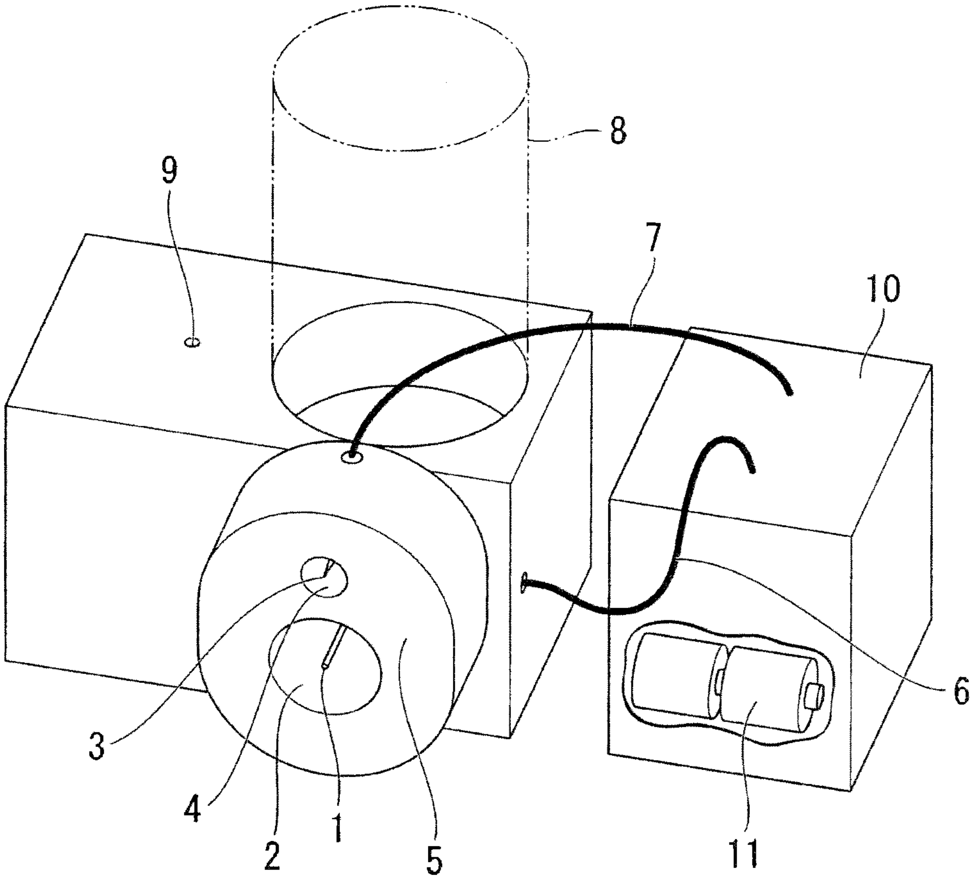
8
9
7
10
6
3
4
2
1
5
11

METHOD OF CONTROLLING HARMFUL ARTHROPOD, COMPOSITION, AND ELECTROSTATIC SPRAY DEVICE

This Nonprovisional application claims priority under 35 U.S.C. §119(a) on Patent Applications No. 2011-004037 filed in Japan on Jan. 12, 2011, No. 2011-011398 filed in Japan on Jan. 21, 2011, No. 2011-014408 filed in Japan on Jan. 26, 2011, No. 2011-014409 filed in Japan on Jan. 26, 2011, No. 2011-014410 filed in Japan on Jan. 26, 2011, and No. 2011-014411 filed in Japan on Jan. 26, 2011, the entire contents of which are hereby incorporated by reference.

TECHNICAL FIELD

The present invention relates to (i) a method of controlling a harmful arthropod such as a flying insect, (ii) a composition, and (iii) an electrostatic spray device.

BACKGROUND ART

Ester compounds represented by the following formulas (1) through (5), respectively, have been known as being effective in controlling a pest, and have been disclosed in Patent Literatures 1 through 4. In the present invention, hereinafter, pests which are targets to be controlled, more specifically, arthropods including insects, are referred to as "harmful arthropods", in some cases. Further, in the present specification, the wording "controlling a harmful arthropod" means to change action of the harmful arthropod by repelling, attracting, knocking down, or killing the harmful arthropod. Furthermore, the wording "effective in controlling" means to supply an active constituent in such an amount that the action of the harmful arthropod can be changed.

(1)

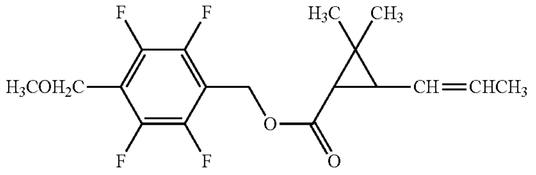

(2)

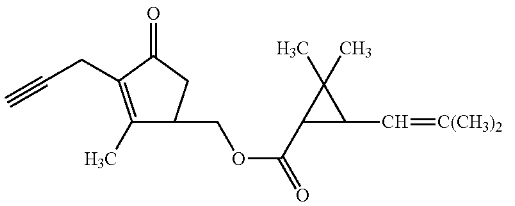

(3)

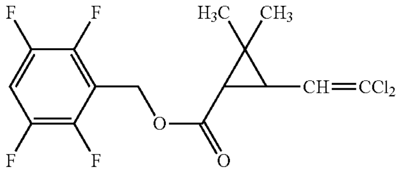

-continued (4)

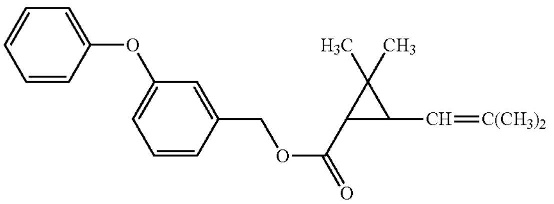

(5)

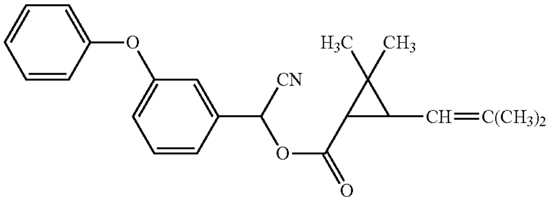

Generally, in order to control a harmful arthropod, an active constituent having an effect of controlling the harmful arthropod is diffused through a heating process (such as a smoking process), a pressure process (such as a gas-pressure process and a mechanical pressure process), or the like, so as to cause the harmful arthropod and the active constituent to be in contact with each other either directly or indirectly and either continuously or intermittently.

Further, an electrostatic spraying technique has been known in this technical field (see Patent Literature 5 and Non-patent Literature 1, for example). According to the electrostatic spraying technique, a Taylor cone of a liquid is formed, and then liquid particles of the liquid are sprayed from an end of the Taylor cone.

CITATION LIST

Patent Literature

[Patent Literature 1]
Japanese Patent Application Publication, Tokukaihei, No. 11-222463 A (1999) (Publication Date: Aug. 17, 1999)
[Patent Literature 2]
Japanese Patent Application Publication, Tokukaisho, No. 49-54529 A (1974) (Publication Date: May 27, 1974)
[Patent Literature 3]
Japanese Patent Application Publication, Tokukaisho, No. 63-203649 A (1988) (Publication Date: Aug. 23, 1988)
[Patent Literature 4]
Japanese Patent Application Publication, Tokukaisho, No. 53-91125 A (1978) (Publication Date: Aug. 10, 1978)
[Patent Literature 5]
Specification of European Patent Application Publication No. 1399265

Non-Patent Literature

[Non-Patent Literature 1]
Proceedings of the Royal Society—1964, p 383-397

SUMMARY OF INVENTION

Technical Problem

There has been demand for (i) a method of controlling a harmful arthropod by efficiently spraying one of the ester compounds represented by the aforementioned formulas (1) through (5), respectively, and (ii) a composition which can be sprayed efficiently.

The present invention is made in view of the problems. An object of the present invention is to provide a method of controlling a harmful arthropod, which method makes it possible to carry out a control process effectively without carrying out any heating process (e.g., a smoking process) for spraying a composition or any pressure process (e.g., a gas-pressure process or a mechanical pressure process) for spraying the composition. Further, another object of the present invention is to provide a composition which can be used to control a wide variety of sorts of harmful arthropod. Furthermore, still another object of the present invention is to provide an electrostatic spray device which (i) can easily spray the composition of the present invention without carrying out any heating process for spraying the composition or any pressure process for spraying the composition, and (ii) can carry out a process of controlling a harmful arthropod effectively.

Solution to Problem

In order to attain the object, a method of the present invention, for controlling a harmful arthropod, includes the step of: electrostatically spraying, to the harmful arthropod or an area where the harmful arthropod inhabits, a composition in an amount which is effective in controlling the harmful arthropod, the composition containing at least one of ester compounds represented by the following formulas (1) through (5), respectively:

(1)

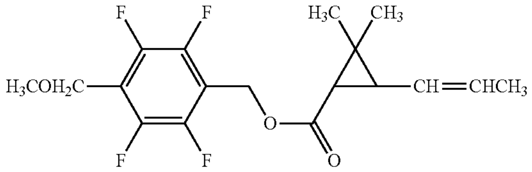

(2)

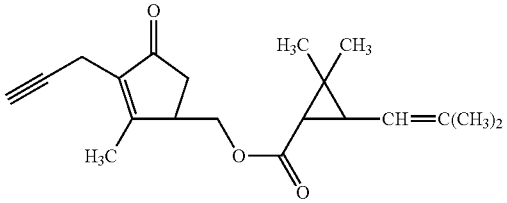

(3)

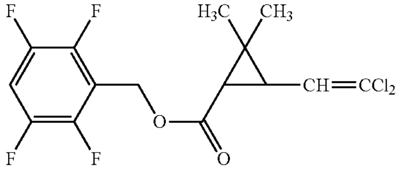

(4)

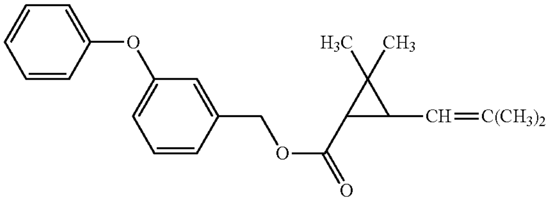

-continued (5)

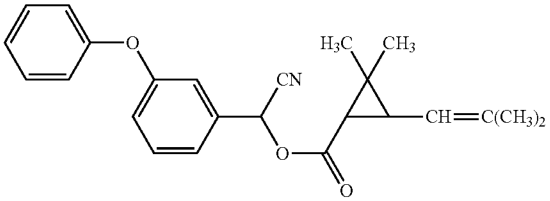

Further, a composition of the present invention includes at least one of ester compounds represented by the following formulas (1) through (5), respectively, the composition having (i) an electric resistance of not less than $1\times10^3$ Ωm but not more than $1\times10^6$ Ωm at a temperature of 20° C., (ii) a viscosity of not less than 1 mPa·s but not more than 10 mPa·s at a temperature of 20° C., and (iii) a surface tension of not less than 20 mN/m but not more than 40 mN/m at a temperature of 20° C.:

(1)

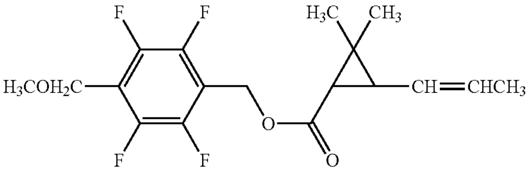

(2)

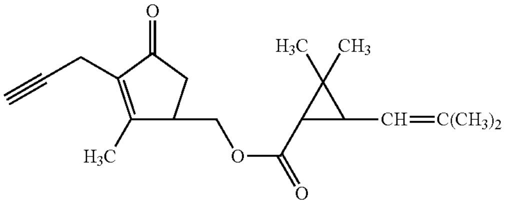

(3)

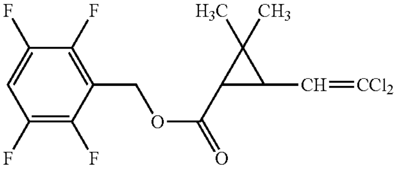

(4)

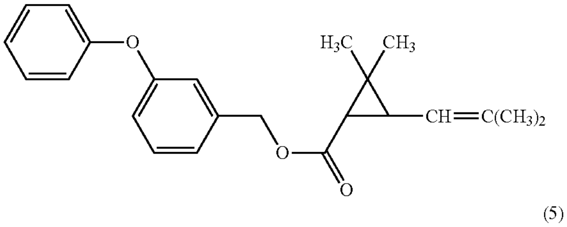

(5)

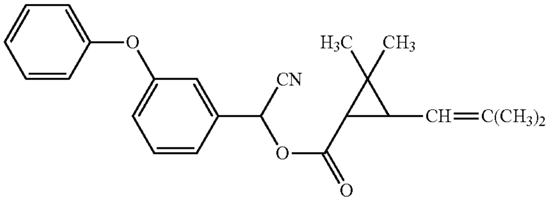

Advantageous Effects of Invention

According to a control method of the present invention, it is possible to carry out a control process effectively without carrying out any heating process (e.g., a smoking process) for spraying a composition or any pressure process (e.g., a gas-pressure process or a mechanical pressure process) for spraying the composition. Further, according to a composition of the present invention, it is possible to control a wide variety of sorts of harmful arthropod. Furthermore, according to an electrostatic spray device of the present invention, it is possible to (i) spray the composition of the present invention easily without carrying out any heating process for spraying the composition or any pressure process for spraying the composition, and (ii) carry out a process of controlling a harmful arthropod effectively.

BRIEF DESCRIPTION OF DRAWINGS

FIG. 1 is a view schematically illustrating an electrostatic spray device which is used to spray a composition in accordance with an embodiment of the present invention.

DESCRIPTION OF EMBODIMENTS

One embodiment of the present invention is described below.

A composition of the present embodiment is suitably used in a method of the present embodiment, for controlling a harmful arthropod, as described below. The composition of the present embodiment contains (i) at least one of ester compounds represented by respective formulas (1) through (5) and (ii) a dispersion medium. A substance that can be used as the dispersion medium may contain a dispersion medium (hereinafter, referred to as "physical property adjustment component" in some cases) that has a function of adjusting a physical property of the composition (such as an electric resistance, a viscosity, and a surface tension).

(Ester Compound)

The composition of the present embodiment contains at least one of the ester compounds represented by the respective formulas (1) through (5). Each of the ester compounds is a compound having an excellent effect of controlling a harmful arthropod.

(1)

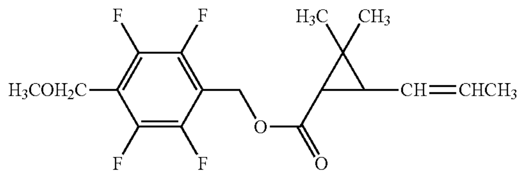

The ester compound represented by the formula (1) is [2,3,5,6-tetrafluoro-4-(methoxymethyl)phenyl]methyl=2,2-dimethyl-3-(1-propenyl)cyclopropane carboxylate. The ester compound represented by the formula (1) can be prepared in accordance with a method described in Japanese Patent Application Publication, Tokukaihei, No. 11-222463 A (1999), for example.

As to the ester compound represented by the formula (1), there are three sorts of isomer, namely, (i) isomers (R-isomer, S-isomer) derived from two asymmetric carbon atoms existing on a cyclopropane ring, (ii) isomers (cis-isomer, trans-isomer) derived from a steric structure defined by a cyclopropane ring, and (iii) isomers (E-isomer, Z-isomer) derived from a double-bond in a substituent group on a cyclopropane ring. The ester compound of the present invention may contain active isomers at an arbitrary content ratio. The content ratio of such active isomers in the ester compound of the present invention is determined in accordance with stereoselectivity of reaction carried out to prepare the ester compound of the present invention, for example. Further, it is also possible that (i) such active isomers are mixed with each other at an arbitrary ratio, and (ii) the ester compound of the present invention contains a mixture thus obtained.

Examples of the ester compound represented by the formula (1) encompass [2,3,5,6-tetrafluoro-4-(methoxymethyl)phenyl]methyl=(1R)-2,2-dimethyl-3-(1-propenyl)cyclopropane carboxylate, [2,3,5,6-tetrafluoro-4-(methoxymethyl)phenyl]methyl=(1R)-trans-2,2-dimethyl-3-(1-propenyl)cyclopropane carboxylate, [2,3,5,6-tetrafluoro-4-(methoxymethyl)phenyl]methyl=(1R)-cis-2,2-dimethyl-3-(1-propenyl)cyclopropane carboxylate, [2,3,5,6-tetrafluoro-4-(methoxymethyl)phenyl]methyl=(1R)-trans-2,2-dimethyl-3-((E)-1-propenyl)cyclopropane carboxylate, [2,3,5,6-tetrafluoro-4-(methoxymethyl)phenyl]methyl=(1R)-trans-2,2-dimethyl-3-((Z)-1-propenyl)cyclopropane carboxylate, and [2,3,5,6-tetrafluoro-4-(methoxymethyl)phenyl]methyl=(1R)-trans-2,2-dimethyl-3-((E/Z=1/8)-1-propenyl)cyclopropane carboxylate. Among these, the ester compound represented by the formula (1) is preferably a (1R)-trans isomer.

Note that, in the ester compound represented by the formula (1), a carbon atom to which a carboxyl group is bound is at a 1 position in the cyclopropane ring, and a carbon atom to which a substituent group having a carbon-carbon double-bond is bound is at a 3 position in the cyclopropane ring.

An amount of such an ester compound in the composition is in a range of approximately 0.1% by mass to approximately 10% by mass, preferably in a range of 0.2% by mass to 8% by mass, more preferably 1.0% by mass to 6% by mass.

(2)

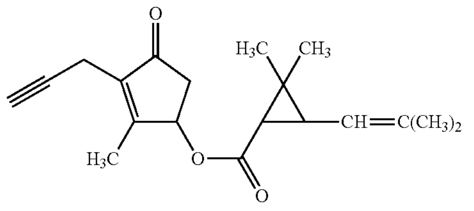

The ester compound represented by the formula (2) is 2-methyl-4-oxo-3-(2-propynyl)-2-cyclopentenyl=2,2-dimethyl-3-(2-methyl-1-propenyl)cyclopropane carboxylate. The ester compound represented by the formula (2) can be prepared in accordance with a method described in Japanese Patent Application Publication, Tokukaisho, No. 49-54529 A (1974), for example.

As to the ester compound represented by the formula (2), there are (i) isomers derived from two asymmetric carbon atoms existing on a cyclopropane ring and (ii) isomers derived from an asymmetric carbon atom existing on a five-membered ring. The ester compound of the present invention can contain such active isomers at an arbitrary content ratio.

An amount of such an ester compound in the composition is not less than approximately 0.1% by mass but not more than approximately 10% by mass, preferably not less than 0.6% by mass but not more than 8% by mass, more preferably not less than 1.0% by mass but not more than 6% by mass.

(3)

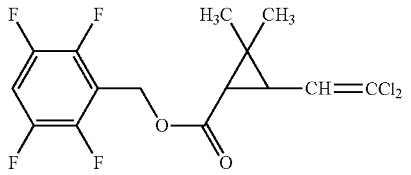

The ester compound represented by the formula (3) is (2,3,5,6-tetrafluorophenyl)methyl=3-(2,2-dichlorovinyl)-2,2-dimethyl-cyclopropane carboxylate. The ester compound represented by the formula (3) can be prepared in accordance with a method described in Japanese Patent Application Publication, Tokukaisho, No. 63-203649 A (1988), for example.

As to the ester compound represented by the formula (3), there are isomers derived from two asymmetric carbon atoms on the cyclopropane ring. The ester compound of the present invention can contain such active isomers at an arbitrary content ratio.

An amount of such an ester compound in the composition is not less than approximately 0.1% by mass but not more than approximately 10% by mass, preferably not less than 0.2% by mass but not more than 8% by mass, more preferably not less than 1.0% by mass but not more than 6% by mass.

(4)

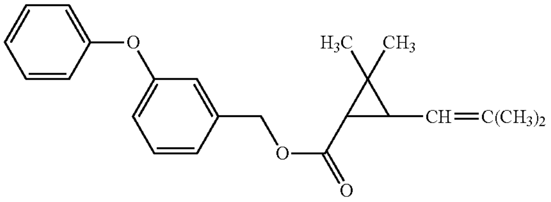

The ester compound represented by the formula (4) is 3-phenoxybenzyl=2,2-dimethyl-3-(2-methyl-1-propenyl) cyclopropane carboxylate. The ester compound represented by the formula (4) can be prepared in accordance with a method described in Japanese Patent Application Publication, Tokukaisho, No. 53-91125 A (1978), for example.

As to the ester compound represented by the formula (4), there are isomers derived from two asymmetric carbon atoms on the cyclopropane ring. The ester compound of the present invention can contain such active isomers at an arbitrary content ratio.

An amount of such an ester compound in the composition is not less than approximately 0.1% by mass but not more than approximately 10% by mass, preferably not less than 0.6% by mass but not more than 8% by mass, more preferably not less than 1.0% by mass but not more than 6% by mass.

(5)

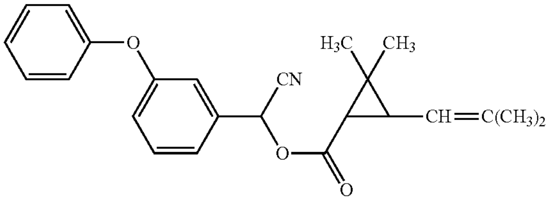

The ester compound represented by the formula (5) is α-cyano-3-phenoxybenzyl=2,2-dimethyl-3-(2-methyl-1-propenyl)cyclopropane carboxylate. The ester compound represented by the formula (5) can be prepared in accordance with a method described in Japanese Patent Application Publication, Tokukaisho, No. 53-91125 A (1978), for example.

As to the ester compound represented by the formula (5), there are two sorts of isomer, namely: (i) isomers derived from two asymmetric carbon atoms on the cyclopropane ring and (ii) isomers derived from an asymmetric carbon atom at a benzyl position. The ester compound of the present invention can contain such active isomers at an arbitrary content ratio.

An amount of such an ester compound in the composition is not less than approximately 0.1% by mass but not more than approximately 10% by mass, preferably not less than 0.6% by mass but not more than 8% by mass, more preferably not less than 1.0% by mass but not more than 6% by mass.

(Dispersion Medium)

The composition of the present embodiment contains a dispersion medium which causes at least one of the ester compounds represented by the respective formulas (1) through (5) to be dissolved or dispersed. The dispersion medium is a solvent (such as an organic solvent) or a solvent mixture (such as an organic solvent mixture). The solvent may be either a polar solvent or a nonpolar solvent. Generally, a polar solvent is suitably used as the solvent.

In the present embodiment, in order to spray the composition effectively, an electrostatic spray device is used to (i) cause the composition to be in a form of stable small droplets (later described) and (ii) spray such droplets. Accordingly, it is desirable that the composition has the following properties: (i) at least one of the compounds represented by the respective formulas (1) through (5) is uniformly dispersed or dissolved in the composition, (ii) the composition has an appropriate electric resistance, an appropriate viscosity, and an appropriate surface tension, and (iii) the dispersion medium is low in toxicity.

Appropriate examples of the dispersion medium of the composition encompass (i) a dispersion medium containing a polyol which has at least one hydroxy group per molecule (such as ethyl alcohol, propylene glycol, triethylene glycol, glycerine, polyethylene glycol, and polypropylene glycol), and (ii) a dispersion medium containing a polyolether which has at least one hydroxyl group per molecule (such as glycol ether (e.g., glycol methyl ether)). As the polyolether, dipropylene glycol methyl ether is suitably used in particular. Other than dipropylene glycol methyl ether, particularly suitable examples of the polyolether encompass propylene glycol methyl ether and tripropylene glycol methyl ether.

Other than these, the dispersion medium may be 1-methoxy-2-propanol acetic ester, 1-buthoxy-2-propanol, 1-propoxy-2-acetoxypropane, or oxybis(methoxy)propane.

An amount of such a dispersion medium in the composition is preferably not less than 65% by mass but not more than 99.9% by mass, more preferably not less than 65% by mass but not more than 99% by mass, further more preferably not less than 70% by mass but not more than 95% by mass. It is possible that an amount of such a dispersion medium in the composition is not less than 90% by mass but not more than 99% by mass, and it is also possible that an amount of such a dispersion medium in the composition is not less than 90% by mass but not more than 99.9% by mass.

There is a case where the dispersion medium used in the composition of the present embodiment serves as a physical property adjustment component. By using such a physical property adjustment component appropriately, it is possible to adjust a physical property of the composition of the present embodiment. In this case, it is possible to use either a single physical property adjustment component or a plurality of physical property adjustment components in combination with each other.

Examples of the physical property adjustment component encompass an ester solvent, a petroleum solvent (such as a paraffinic solvent, an aromatic solvent, and a naphthenic solvent) (e.g., Isopar L (registered trademark)), silicone oil (such as decamethyltetrasiloxane, decamethylcyclopentasiloxane, dodecamethylcyclohexasiloxane, and a mixture of these), polyethylene glycol, water, and a dilute aqueous solution of an electrolyte (such as a dilute aqueous solution of sodium hydrogen carbonate, sodium acetate, sodium chloride, ascorbic acid, citric acid, or acetic acid).

For example, in some cases, by adding isoparaffin (such as Isopar L) to the composition, it is possible to reduce the surface tension of the composition. In the present specification, a component having an effect of adjusting the surface tension of the composition is referred to as "surface tension adjustment component". Note that the composition can contain isoparaffin in an amount in a range of 0% by mass to 9.99% by mass, for example.

Further, in some cases, by adding, to the composition, polyethylene glycol ("PEG") having an average molecular weight of more than 200 Da (e.g., a relatively low average molecular weight of not less than 200 Da but not more than 700 Da), it becomes possible to adjust the composition in viscosity. In the present specification, a component having an effect of adjusting the viscosity of the composition is referred to as "viscosity adjustment component", in some cases.

Furthermore, by adding an electrolyte to the composition, it is possible to adjust the composition in electric resistance. In the present specification, a component having an effect of adjusting the electric resistance is referred to as "resistivity adjustment component", in some cases. An appropriate electrolyte used for such a purpose has been known in this technical field. For example, the electrolyte may be a dilute aqueous solution of alkanoic acid salt such as a dilute solution of sodium acetate (e.g., a 0.4% by mass sodium acetate solution), or the aforementioned dilute aqueous solution of the electrolyte.

Further, a dispersion medium (resistivity adjustment component) which can be used to adjust the composition in electric resistance may be a surfactant (such as a nonionic surfactant, an ampholytic surfactant, an anionic surfactant, and a cationic surfactant).

Examples of the nonionic surfactant that can be contained in the composition of the present invention encompass sorbitan fatty acid ester (such as sorbitan stearate, and sorbitan oleate), glycerin fatty acid ester (such as glyceryl stearate, glyceryl isostearate, glyceryl oleate, polyglyceryl stearate, polyglyceryl isostearate, and polyglyceryl oleate), polyoxyethylene alkyl ether (such as polyoxyethylene lauryl ether, polyoxyethylene cetyl ether, polyoxyethylene stearyl ether, polyoxyethylene oleyl ether, and polyoxyethylene styrylphenyl ether), polyoxyethylene sorbitan fatty acid ester (such as polyoxyethylene sorbitan coconut oil fatty acid, polyoxyethylene sorbitan oleate, and polyoxyethylene sorbitan stearate), and polyoxyethylene sorbitol fatty acid ester (such as polyoxyethylene sorbitol tetraoleate). Other than these, the nonionic surfactant may be polyoxyethylene hydrogenated castor oil, alkylphenol polyglycol ether, or the like.

Examples of the ampholytic surfactant that can be contained in the composition of the present embodiment encompass betaine (such as lauryl betaine, and stearyl betaine), and imidazoline derivatives (such as di-sodium N-lauryl-p-iminodipropionate). Other than these, the ampholytic surfactant may be lecithin or the like.

Examples of the anionic surfactant that can be contained in the composition of the present embodiment encompass alkyl sulfate (such as sodium lauryl sulfate and triethanolamine lauryl sulfate), polyoxyethylene alkyl ether sulfate such as (sodium polyoxyethylene lauryl ether sulfate and triethanolamine polyoxyethylene lauryl ether sulfate), alkylbenzene sulfonate (such as sodium dodecylbenzene sulfonate), and polyoxyethylene alkyl ether phosphate (such as sodium dipolyoxyethylene lauryl ether phosphate, and sodium dipolyoxyethylene oleyl ether phosphate).

Examples of the cationic surfactant that can be contained in the composition of the present embodiment encompass alkyl ammonium salt (such as cetyltrimethylammonium chloride and distearyldimethylammonium chloride).

Further, as the dispersion medium that can be used to adjust the composition of the present embodiment in electric resistance, it is possible to add, to the composition of the present embodiment, salt of quaternary amine other than the ones described above, a preservation agent, and salt of chlorhexidine (such as chlorhexidine digluconate), and/or other air-cleaning agents (including the ones disclosed in the present specification).

Further, in a case where the dispersion medium is a polyolether, properties of the composition described above meet the conditions described above. For this reason, it is preferable that (i) the composition contains (I) at least one of the ester compounds represented by the respective formulas (1) through (5), and (II) the dispersion medium for dispersing the at least one of the ester compounds, and (ii) the dispersion medium contains the followings: (a) a low-vapor pressure component containing (1) at least one compound selected from the group consisting of a polyolether represented by the following general formula (6) (hereinafter, merely referred to as "polyolether"), and a dibasic ester, and, optionally, (2) dipropylene glycol; (b) a resistivity adjustment component, and, optionally, (c) a surface tension adjustment component. Note that the resistivity adjustment component and the surface tension adjustment component serve as "physical property adjustment component" of the present specification.

$$R^1O—[CH_2CH(CH_3)O]_n—H \quad (6)$$

Furthermore, it is preferable that such a composition has a vapor pressure of less than 14 Pa at a temperature of 20° C.

In the specification and Claims of the subject application, the term "vapor pressure" means a vapor pressure measured for a composition from which an arbitrary aqueous component is excluded, which vapor pressure is measured in accordance with Air Resource Board Method 310, "Determination of Volatile Organic Compounds (VOC) in Consumer Products" (ARB method 310). Note that the "VOC" is an organic compound which boils, at a standard pressure, at a temperature in a range up to approximately 260° C.

According to the composition of the present embodiment, the low-vapor pressure component contains (i) at least one compound selected from the group consisting of a polyolether and a dibasic ester, and, optionally, (ii) dipropylene glycol. That is, the low-vapor pressure component contains, as an essential component, one of, or both of a polyolether and a dibasic ester, and, if necessary, can further contain dipropylene glycol as an optional component.

In the aforementioned general formula (6) representing the polyolether, $R^1$ is a $C_1$ to $C_4$ alkyl group, and the $C_1$ to $C_4$ alkyl group may be a linear, branched, or cyclic alkyl group. Note, however, that it is preferable that the $C_1$ to $C_4$ alkyl group is a linear or branched alkyl group. Specifically, examples of the $C_1$ to $C_4$ alkyl group encompass a methyl group, an ethyl group, an n-propyl group, an isopropyl group, an n-butyl group, an isobutyl group, a sec-butyl group, and a tert-butyl group.

Further, in the aforementioned general formula (6), n is 2 or 3. Note, however, that, in a case where n is 2, $R^1$ is not a methyl group.

Examples of the polyolether encompass dipropylene glycol ethyl ether, dipropylene glycol-n-propyl ether (hereinafter, merely referred to as "DPnP", in some cases), dipropylene glycol-n-butyl ether, tripropylene glycol methyl ether, tripropylene glycol ethyl ether, and tripropylene glycol-n-propyl ether. Among these, dipropylene glycol-n-propyl ether is suitably used as the polyolether.

It is possible to employ either one sort of polyolether or two or more sorts of polyolether in combination with each other.

Examples of the dibasic ester (hereinafter, merely referred to as "DBE", in some cases) encompass dimethyl glutarate and dimethyl adipate.

It is possible to employ either one sort of dibasic ester or two or more sorts of dibasic ester in combination with each other.

According to the present invention, it is preferable that the dibasic ester is at least one sort selected from the group consisting of dimethyl glutarate and dimethyl adipate.

In a case where the dibasic ester is a mixture of dimethyl glutarate and dimethyl adipate, it is preferable that a content ratio of dimethyl glutarate in the mixture is not less than 5% by mass but not more than 80% by mass with respect to a total amount of the mixture, and a content ratio of dimethyl adipate is not less than 20% by mass but not more than 95% by mass with respect to the total amount of the mixture.

An amount of the low-vapor pressure component in the composition of the present embodiment is not less than 10% by mass but not more than 98.9% by mass, preferably not less than 75% by mass but not more than 98.9% by mass with respect to a total amount of the composition.

In a case where the composition of the present embodiment contains the polyolether, an amount of the polyolether in the composition is not less than 10% by mass but not more than 99.9% by mass, preferably not less than 20% by mass but not more than 95% by mass, more preferably not less than 30% by mass but not more than 90% by mass with respect to the total amount of the composition.

In a case where the composition of the present invention contains the dibasic ester, an amount of the dibasic ester in the composition of the present invention is not less than 10% by mass but not more than 99.9% by mass, preferably not less than 20% by mass but not more than 95% by mass, more preferably not less than 30% by mass but not more than 90% by mass with respect to the total amount of the composition.

In a case where the composition of the present invention contains dipropylene glycol, an amount of dipropylene glycol in the composition of the present invention is not less than 10% by mass but not more than 99.9% by mass, preferably not less than 20% by mass but not more than 95% by mass, more preferably not less than 30% by mass but not more than 90% by mass with respect to the total amount of the composition.

As the resistivity adjustment component, it is possible to employ a component having an effect of adjusting a resistivity of the composition, which component has been known by a person skilled in the art. Examples of the resistivity adjustment component encompass the resistivity adjustment components described above.

For example, water contains an electrolyte in a significantly small amount, and typically has a resistivity of not less than $1\times10^1$ Ωm, more typically a resistivity of not less than $1\times10^3$ Ωm, further more typically a resistivity of not less than $1\times10^4$ Ωm, most typically a resistivity of not less than $1\times10^5$ Ωm. For example, water is likely to have a resistivity of not less than $1\times10^6$ Ωm, or not less than $1\times10^7$ Ωm.

According to the present invention, it is preferable that water used as the resistivity adjustment component has a purity equal to or more than that of deionized water, or that of water.

The electrolyte can be added to the composition as an aqueous solution, for example. Examples of the electrolyte encompass the electrolytes described above.

In a case where the composition of the present invention contains the electrolyte, an amount of the electrolyte in the composition of the present invention is preferably not less than 0.5% by mass but not more than 10% by mass, more preferably not less than 1% by mass but not more than 8% by mass with respect to the total amount of the composition.

It is possible to employ either one sort of resistivity adjustment component or two or more sorts of resistivity adjustment component in combination with each other.

In a case where the composition of the present invention contains the resistivity adjustment component, an amount of the resistivity adjustment component in the composition of the present invention is preferably not less than 0.5% by mass but not more than 5% by mass, more preferably not less than 0.7% by mass but not more than 4.5% by mass, further more preferably not less than 1% by mass but not more than 4% by mass with respect to the total amount of the composition.

Examples of the surface tension adjustment component encompass isoparaffin (such as Isopar L), and silicone oil (such as decamethyltetrasiloxane, decamethylcyclopentasiloxane, dodecamethylcyclohexasiloxane, and a mixture of these).

It is possible to employ either one sort of surface tension adjustment component or two or more sorts of surface tension adjustment component.

In a case where the composition of the present invention contains the surface tension adjustment component, an amount of the surface tension adjustment component in the composition of the present invention is not less than 0.5% by mass but not more than 10% by mass, preferably not less than 1% by mass but not more than 10% by mass, more preferably not less than 2% by mass but not more than 10% by mass, further more preferably not less than 3% by mass but not more than 10% by mass with respect to the total amount of the composition.

The composition of the present invention can contain another component other than the ester compound, the low-vapor pressure component, the resistivity adjustment component, and the surface tension adjustment component.

Examples of the another component encompass a viscosity adjustment component. For example, by adding polyethylene glycol or glycerine described above to the composition, it is possible to increase the composition in viscosity.

Further, the composition of the present invention can contain a fluorescent agent in such a small amount that the fluorescent agent has no significant influence on an entire property of the composition. For example, the composition of the present invention can contain 1% by mass or less of Uvitex-OB or the like.

In a case where such a composition has a vapor pressure of less than 14 Pa at a temperature of 20° C., the composition used to control a harmful arthropod would comply with the regulations on contents of VOC. For example, according to Consumer Production Regulation, (Article 2) of California in the U.S., no person shall sell, supply, offer for sale, or manufacture for sale in California any consumer product which, at the time of sale or manufacture, contains volatile organic compounds in excess of the specified limits. The composition described above can comply with such regulations.

In order to measure physical properties of the composition described above, the following methods and devices are used.

First, an electric resistance of the composition can be measured by use of a resistivity meter (pH/ION/COND METER F-55, manufactured by HORIBA, Ltd.) with a liquid resistivity cell. A unit of a value obtained through the measurement is "MΩ·m".

Further, a surface tension of the composition can be measured by use of a contact angle/surface tension meter (DM-501, manufactured by Kyowa Interface Science Co., LTD) whose measurement principle is based on a pendant-drop method. A unit of a value obtained through the measurement is "mN/m".

Furthermore, a viscosity of the composition can be measured by use of a rotational viscometer (RB85L, manufactured by TOKI SANGYO CO., LTD.). A unit of a value obtained through the measurement is "mPa·s". As a method of the measurement, a method in accordance with "JIS Z8803 Viscosity of liquid-Methods of measurement" can be employed.

A diameter of liquid droplets of the composition, obtained after the composition is sprayed, can be measured as "average particle diameter" by use of particle size distribution measurement device (Aero Particle Sizer Model 3321, manufactured by TSI Instruments Inc. or Scanning Mobility Particle Sizer Model 3936, manufactured by TSI Instruments Inc.). A unit of a value obtained through the measurement is "nm" or "μm". Note that, for an average particle diameter of not less than 100 nm but not more than 500 nm (i.e., ·0.5 μm), a value obtained by use of Model 3936 was used, while, for an average particle diameter of more than 0.5 μm but not more than 10 μm, a value obtained by use of Model 3321 was used.

The composition can be adjusted in electric resistance appropriately so that the electric resistance is not less than $1\times10^3$ Ωm but not more than $1\times10^6$ Ωm at a temperature of 20° C. Further, the composition can be adjusted in viscosity appropriately so that the viscosity is not less than 1 mPa·s but not more than 10 mPa·s at a temperature of 20° C. Furthermore, the composition can be adjusted in surface tension appropriately so that the surface tension is not less than 20 mN/m but not more than 40 mN/m at a temperature of 20° C. By setting the composition to have properties in the ranges described above, it becomes possible to spray successfully the composition by use of an electrostatic spray device (later described).

In addition to the components described above, the composition used in the present invention can further contain a perfume or an air-cleaning agent, as an additional component.

The perfume may be an essential oil or another fragrance oil, for example. As the perfume, it is possible to use only a part of all fractions (oil components) contained in such an oil.

More specifically, preferable examples of the perfume encompass Melaleuca oil, tea tree oil (such as terpinene-4-ol), catmint oil (such as *Nepeta Cataria* and a refined oil of *Nepeta Cataria*), a fraction of catmint oil (such as a fraction containing nepetalactone), thymus oil (such as an oil of *Thymus Vulgaris*), and a fraction of thymus oil (such as a fraction containing thymol).

Further, the perfume such as a fragrance oil is typically, for example, (i) a mixture of different sorts of compound, whose backbones are different from each other in chain length, or (ii) a mixture containing different sorts of stereoisomeric form. It is possible for the composition to contain such a fragrance oil.

Among the examples described above, the perfume preferably includes an oil component of at least one sort selected from the group consisting of tea tree oil, catmint oil, and *Thymus* oil.

In a case where the composition of the present invention contains a fragrance oil, an amount of the fragrance oil in the composition is preferably in a range of 5% by mass to 35% by mass with respect to the total amount of the composition.

Further, it is preferable that the fragrance oil has a vapor pressure of not more than 270 Pa at a temperature of 20° C.

Specific examples of the air-cleaning agent encompass an active air-cleaning component, an active antibacterial component, an active antifungal component, and an active antiallergenic component.

Here, the "active air-cleaning component" is a substance having deodorizing activity.

The "active antibacterial component" is a substance having inhibiting activity of bacterial growth.

The "active antifungal component" is a substance having inhibiting activity of fungal growth.

The "active antiallergenic component" is a substance which inhibits the allergenic activity of an allergen.

As such an air-cleaning agent, it is possible to use either (i) a substance which develops a single function among the functions described above (i.e., one of the functions of the active air-cleaning component, the active antibacterial component, the active antifungal component, and the active antiallergenic component) or (ii) a substance which is expected to develop a plurality of functions among the functions described above. Specifically, preferable examples of the substance which is expected to develop, as the air-cleaning agent, such plurality of functions, encompass a polyhexamethylene bi-guanido polymer, a polyhexamethyl guanido polymer, alkyl dimethyl benzyl ammonium chloride, octyl decyl dimethyl ammonium chloride, chlorhexidine, chlorhexidine digluconate, benzalkonium chloride, sodium hypochlorite, 2-phenylphenol, polyethylene glycol 300, 2-benzyl-4-chlorophenol, 2-phenoxyethanol, glutaraldehyde, phthalaldehyde, chloroxylenol, trichlorophenol, phenol, silver salt (particularly, water-soluble silver salt), hexachlorophene, peracetic acid, lactic acid, performic acid, potassium permanganate, and potassium peroxymonosulfate.

In a case where the composition of the present invention contains the air-cleaning agent, an amount of the air-cleaning agent in the composition is preferably not less than 0.05% by mass but not more than 20% by mass, more preferably not less than 0.1% by mass but not more than 17% by mass, further more preferably not less than 0.1% by mass but not more than 15% by mass with respect to the total amount of the composition.

Examples of the active antibacterial component encompass triclosan, trichlorocarbanilide, isopropylmethylphenol, N-(dichloro fluoromethylthio)-phthalamide, N'-(dichloro fluoromethylthio) N,N'-dimethyl-N'-phenyl-sulphamide, polyoctyl polyaminoethylglycine, thiabendazole, chlorine dioxide, 2-bromo-2-nitroethanol, 2-bromo-2-nitropropane-1,3-diol, 2-bromo-2-nitropropanol, 1-bromo-1-nitro propanol, 1,4-dibromo-1,4-dinitro butanediol-2,3-cetylpyridinium, 1-bromo-1-nitro-2-methyl propanol-2-cetylpyridinium, cetylpyridinium chloride, benzethonium chloride, acrinol, povidone-iodine, mercurochrome, chloramphenicol, fradiomycin sulfate, gentamycin sulfate, oxytetracycline hydrochloride, polymyxin B sulfate, trichomycin, and griseofulvin.

Examples of the active antifungal component encompass benzoic acid, salt of benzoic acid, sorbic acid, salt of sorbic acid, paraoxybenzoic esters, sodium dehydroacetate, propionic acid, polylysine, thiabendazole, terpene alcohol (such as linalool, geraniol, nerol, citronellol, α-terpineol, terpinene-4-ol, and isopulegol), $C_7$ to $C_{15}$ alicyclic alcohol (such as 2,4-dimethyl-3-cyclohexene-1-methanol, 4-isopropylcyclohexanol, 4-isopropylcyclohexanemethanol, 1-(4-isopropylcyclohexyl)-ethanol, and 2,2-dimethyl-3-(3-methylphenyl)-propanol), and $C_7$ to $C_{15}$ arylalkyl alcohol (or $C_7$ to $C_{15}$ alkylaryl alcohol) (such as benzyl alcohol, phenylethyl alcohol, phenyl propyl alcohol, carvacrol, and eugenol).

Examples of the active antiallergenic component encompass hydroxyapatite, epicatechin, epigallocatechin, epicatechin gallate, epigallocatechin gallate, gallic acid, and an ester compound of gallic acid and $C_1$ to $C_4$ alcohol.

Examples of the active air-cleaning component for deodorization or the like encompass tannin, polyphenol (such as flavonoid (e.g., chalkone, flavanone, flavanol, flavone, flavonol, or isoflavone)), cyclodextrin, lauryl methacrylate, geranyl clorinate, 4-hydroxy-6-methyl-3-(4-methylpentanoyl)-2-pyrone, formalin, glyoxal, sodium bisulfite, sodium sulfite, dihydroxyacetone, 3,5,5-trimethyl hexanol, β-ethoxy propionaldehyde, glutaraldehyde, methacrylate ester, maleic acid ester, maleic acid monoamide, maleic acid imide, fumaric acid ester, β-acyl acrylic acid, salt of β-acyl acrylic acid, senecioic acid citronellyl, 1,3-pentadiene-1-carboxylic acid alkyl ester, pinane hyderoperoxide, p-cymeneperoxide, 1,2-propyleneoxide, 1,2-butyleneoxide, glycidyl ether, saccharose octaacetate, Fe(III)-octacarboxyphthalocyanine, Fe(III)-tetracarboxyphthalocyanine, 5-methyl-2-isopropyl-2-hexenol, p-butoxyphenol, catechol, hydroquinone, 4-methylcatechol, 1,2,4-trihydroxybenzene, 3-methylcatechol, 3-methoxycatechol, carnosol, rosmanol, brazilin, hematoxylin, shikonin, myricetin, baicalein, baicalin, citral, vanilline, and coumarin.

The composition of the present embodiment can be the following composition, for example.

TABLE 1

| | Percent by mass |
|---|---|
| (I) Ester compound | 0.1-10 |
| (II) Dispersion medium | 90-99.9 |
| Physical property adjustment component in (II) | 0.5-25 |

Further, a preferable example of the composition in accordance with the present embodiment may be a composition in which the ester compound and the dispersion medium containing the low-vapor pressure component, the resistivity adjustment component, and the surface tension adjustment component are contained at a content ratio shown in the following Table 2.

TABLE 2

| | | Percent by mass |
|---|---|---|
| (I) Ester compound | | 0.1-10 |
| (II) Dispersion medium | | 90-99.9 |
| Low-vapor pressure component in (II) | | 75-98.9 |
| Physical property adjustment component | Resistivity adjustment component in (II) | 0.5-5 |
| | Surface tension adjustment component in (II) | 0.5-10 |

More specifically, a preferable example of the composition of the present embodiment may be a composition in which the ester compound and the dispersion medium containing the low-vapor pressure component, the resistivity adjustment component, and the surface tension adjustment component are contained at a content ratio shown in any one of the following Tables 3 through 6.

TABLE 3

| | | Percent by mass |
|---|---|---|
| (I) Ester compound | | 0.1-10 |
| (II) Dispersion medium | | 90-99.9 |
| Compound represented by general formula (6) (Low-vapor pressure component) in (II) | | 10-98.9 |
| Physical property adjustment component | 0.4% by mass sodium acetate solution | 0.5-5 |
| | Isoparaffin | 0-9.99 |

TABLE 4

| | | Percent by mass |
|---|---|---|
| (I) Ester compound | | 0.1-10 |
| (II) Dispersion medium | | 90-99.9 |
| At least one compound (in (II)) selected from the group consisting of tripropylene glycol monomethyl ether, dipropylene glycol-n-propyl ether, dipropylene glycol-n-butyl ether, and dibasic ester. | | 75-99.4 |
| Physical property adjustment component | Acetate salt | 0.0005-0.1 |
| | Water | 0.49-4.995 |
| | Isoparaffin | 0-9.99 |

TABLE 5

| | | Percent by mass |
|---|---|---|
| (I) Ester compound | | 0.1-10 |
| (II) Dispersion medium | | 90-99.9 |
| Dipropylene glycol-n-propyl ether in (II) | | 10-89.4 |
| Dibasic ester in (II) | | 10-89.4 |
| Physical property adjustment component | Acetate salt | 0.0005-0.1 |
| | Water | 0.49-4.995 |
| | Isoparaffin | 0-9.99 |

TABLE 6

| | | Percent by mass |
|---|---|---|
| (I) Ester compound | | 0.1-10 |
| (II) Dispersion medium | | 90-99.9 |
| Dipropylene glycol-n-propyl ether in (II) | | 10-89.4 |
| Dibasic ester in (II) | | 10-45 |
| Physical property adjustment component | Acetate salt | 0.0005-0.1 |
| | Water | 0.49-4.995 |
| | Isoparaffin | 0-9.99 |

Further, in a case where the composition of the present embodiment contains the additional component described above, the composition of the present embodiment contains its components at a content ratio shown below. First, in a case where the composition of the present invention contains a perfume oil serving as a perfume component, the composition contains the components at the content ratio shown in the following Table 7.

TABLE 7

| | Percent by mass |
|---|---|
| (I) Ester compound | 0.1-10 |
| (II) Dispersion medium | 30-97.9 |
| Physical property adjustment component in (II) | 0.5-25 |
| Perfume oil | 2-60 |

Furthermore, in a case where the composition of the present embodiment contains, as the additional component, a compound for disinfection, the composition of the present embodiment contains its components at a content ratio shown in the following Table 8.

TABLE 8

| | Percent by mass |
|---|---|
| (I) Ester compound | 0.1-10 |
| (II) Dispersion medium | 70-99.8 |
| Physical property adjustment component in (II) | 0.5-25 |
| Air-cleaning agent | 0.1-20 |

(Harmful Arthropod)

Examples of a target to be controlled by use of the composition of the present embodiment encompass arthropods such as insects and ticks, particularly harmful arthropods such as harmful insects and harmful ticks. Specific examples of the target to be controlled by use of the composition of the present embodiment are described below.

Lepidoptera: Pyralidae (such as *Chilo suppressalis, Cnaphalocrocis medinalis, Plodia interpunctella*, and *Ephestia kuehniella*), Fall Armyworm (such as *Spodoptera litura, Pseudaletia separata*, and *Mamestra brassicae*), Pieridae (such as *Pieris rapae*), Tortricidae (such as *Adoxophyes orana*), Carposimidae, Lyonetiidae, Lymantriidae, *Autographa* sp., *Agrotis* spp. (such as *Agrotis segetum*, and *Agrotis ipsilon*), *Helicoverpa* spp., *Heliothis* spp., *Plutella xylostella, Parnara guttata, Tinea translucens, Tineola bisselliella*, etc.

Diptera: *Culex* (such as *Culex pipiens pallens*, and *Culex tritaeniorhynchus*), *Aedes* (such as *Aedes aegypti*, and *Aedes albopictus*), *Anopheles* (such as *Anopheles sinensis*), Chironomidae, Muscidae (such as *Musca domestica, Muscina stabulans*, and *Fannia canicularis*), Calliphoridae, Sarcophagidae, Anthomyiidae (such as *Delia platura, Delia antiqua*), Tephritidae, Agromyzidae, Drosophilidae, Psychodidae, Phoridae, Tabanidae, Simuliidae, Stomoxyini, Ceratopogonidae, etc.

Dictyoptera: *Blattella germanica, Periplaneta fuliginosa, Periplaneta americana, Periplaneta brunnea, Blatta orientalis*, etc.

Hymenoptera: Formicidae (such as *Camponotus japonicus, Tetramorium tsushimae, Lasius japonicus, Pachycondyla chinensis, Monomorium intrudens, Lasius fuji, Monomorium pharaonis, Formica fusca japonica, Ochetellus glaber, Pristomyrmex pungens, Pheidole noda*, and *Linepithema humile*), Polistinae (such as *Polistes chinensis antennalis, Polistes riparius, Polistes jadwigae, Polistes rothneyi, Polistes nipponensis, Polistes snelleni*, and *Polistes japonicus*), Vespidae (such as *Vespa mandarinia japonica, Vespa simillima, Vespa analis insularis, Vespa crabro, Vespa ducalis, Vespula flaviceps, Vespula shidai*, and *Dolichovespula media*), Bethylidae, Tenthredimidae (such as *Athalia japonica*), etc.

Siphonaptera: *Ctenocephalides canis, Ctenocephalides felis, Pulex irritans*, etc.

Anoplura, Phthiraptera: *Pediculus humanus, Phthirus pubis, Pediculus humanus humanus, Pediculus humanus corporis*, etc.

Psocoptera: Psocidae.

Isoptera: Subterranean terminate (such as *Reticulitermes speratus, Coptotermes formosanus, Reticulitermes flavipes, Reticulitermes hesperus, Reticulitermes virginicus, Reticulitermes tibialis*, and *Heterotermes aureus*), Drywood terminate (such as *Incisitermes minor*), Damp-wood terminate (such as *Zootermopsis nevadensis*), etc.

Hemiptera: *Delphacidae* (such as *Laodelphax striatellus, Nilaparvata lugens*, and *Sogatella furcifera*), Cicadellidae (such as *Nephotettix cincticeps*, and *Nephotettix virescens*), Aphididae, Pentatomidae (such as *Nezara antennata, Riptortus clavetus, Eysarcoris lewisi, Eysarcoris parvus, Plautia stali, Halyomorpha mista, Stenotus rubrovittatus*, and *Trigonotylus caelestialium*), Aleyrodidae, Coccoidea, *Cimicidae* (such as *Cimex lectularius*), Tingidae, Psyllidae, etc.

Coleoptera: Corn rootworm (such as *Attagenus japonicus, Anthrenus verbasci, Diabrotica virgifera virgifera*, and *Diabrotica undecimpunctata howardi*), Scarabaeidae (such as *Anomala cuprea* and *Anomala rufocuprea*), Curculionidae (such as *Sitophilus zeamais, Lissorhoptrus oryzophilus, Anthonomus grandis*, and *Callosobruchuys chienensis*), Tenebrionidae (such as *Tenebrio molitor* and *Tribolium castaneum*), *Chrysomelidae* (such as *Oulema oryzae, Phyllotreta striolata*, and *Aulacophora femoralis*), Anobiidae, *Epilachna* spp. (such as *Epilachna vigintioctopunctata*), Lyctidae, Bostrychidae, Ptimidae, Cerambycidae, *Paederus fuscipes*, etc.

Thysanoptera: *Thrips palmi, Frankliniella occidentalis, Thrips nigropilosus*, etc.

Orthoptera: Gryllotalpidae, Acrididae, Gryllidae, etc.

Acarina: Pyroglyphidae (such as *Dermatophagoides farinae* and *Dermatophagoides ptrenyssnus*), Acaridae (such as *Tyrophagus putrescentiae* and *Aleuroglyphus ovatus*), Glycyphagidae (such as *Glycyphagus privates, Glycyphagus domesticus*, and *Glycyphagus destructor*), Cheyletidae (such as *Cheyletus malaccensis, Cheyletus malaccesis*, and *Cheyletus moorei*), Tarsonemidae, Chortoglyphidae, Haplochthoniidae, Tetranychidae (such as *Tetranychus urticae, Tetranychus kanzawai, Panonychus citri*, and *Panonychus ulmi*), Erythraeidae, Ixodidae (such as *Haemaphysalis longicornis*), Dermanyssidae (such as *Ornithonyssus sylvairum* and *Dermanyssus gallinae*), etc.

Scutigeridae, Centipedes (such as *Scolopendra subspinipes*), Diplopoda (such as *Oxidus gracilis* and *Nedyopus tambanus*), Armadillidiidae (such as *Armadillidium vulgare*), Porcellionidae, Gastropoda (such as *Lehmannia valentiana* and *Limax flavus*), Arachnida (such as *Nephila clavata, Chiracanthium japonicum*, and *Latrodectus hasseltii*), etc.

(Control Method)

A method of carrying out a process of controlling a harmful arthropod by use of the composition described above is such that the composition is electrostatically sprayed to a target harmful arthropod to be controlled or to an area where the harmful arthropod inhabits. The electrostatic spraying is carried out by use of an electrostatic spray device.

In the electrostatic spray device, a liquid flows inside a spray electrode having a tube shape. A voltage is applied across the spray electrode and a reference electrode (discharge electrode) provided in the vicinity of the spray electrode. This generates electrostatic force with respect to the liquid flowing inside the spray electrode. Note that positions of the spray electrode and the reference electrode are not particularly limited relatively. For example, it is also possible to provide the spray electrode and the reference electrode so that they face each other. With the electrostatic force, the liquid inside the spray electrode has electrostatic repulsion, so as to be divided into fine particles. When the liquid is sprayed, the liquid is subjected to, for example, a cone jet mode at an end of the spray electrode. Such a spraying method has been well known in this field, as published in Geoffrey Taylor, Proceedings of the Royal Society, 1964, p 383-397. Further, it is preferable that a voltage applied across the spray electrode and the discharge electrode is not less than 1 kV but not more than 30 kV.

An appropriate example of the electrostatic spray device is described in European Patent Application Publication No. 1399265. FIG. 1 illustrates such an example of the electrostatic spray device.

The electrostatic spray device illustrated in FIG. 1 has an arrangement in which (i) a spray electrode 1 having a tube shape is provided inside a depression 2 for the spray electrode 1, which depression 2 is formed on a side surface (spray discharge surface 5) of a main body of the electrostatic spray device, and (ii) a discharge electrode 3 corresponding to the spray electrode 1 is provided inside a depression 4 for the discharge electrode 3, which depression 4 is formed on the side surface (the spray discharge surface 5) of the main body of the electrostatic spray device. From the spray electrode 1, the composition which is charged is sprayed so that the composition is made into particles in a mist form. A voltage opposite to the charge of the composition (the particles in the mist form) is applied to the discharge electrode 3, so that the sprayed particles in the mist form are attracted to the discharge electrode 3. That is, the discharge electrode 3 determines a direction in which the particles in the mist form flow. For example, the spray electrode 1 includes a 27 gauge metal or a conductive plastic capillary, while the discharge electrode 3 includes a sharp-pointed pin made from stainless steel, having a diameter of 0.6 mm.

The spray electrode 1 and the discharge electrode 3 are electrically connected to a driving circuit 10 via respective sheathed metal tubes 6 and 7. With the arrangement, it is possible to apply a voltage so that one of the electrodes serves as a positive electrode and the other one of the electrodes serves as a negative electrode (e.g., the spray electrode 1 serves as a positive electrode, whereas the discharge electrode serves as a negative electrode).

The spray discharge surface 5 is made from a dielectric material. The spray discharge surface 5 of the electrostatic spray device of the present embodiment is made from polypropylene, for example.

Further, the spray discharge surface 5 has the depression 2 in which the spray electrode 1 is provided and the depression 4 in which the discharge electrode 3 is provided, so that the depressions 2 and 4 are arranged in a vertical direction (gravitational direction). According to the electrostatic spray device of the present embodiment, the spray discharge surface 5 is a plane surface, except for parts corresponding to the depressions 2 and 4.

Note, however, that the spray discharge surface 5 is not limited to this. The spray discharge surface 5 may be made from another dielectric material and/or may have a curved surface, provided that (i) the composition in the mist form, sprayed from the spray electrode 1, is sufficiently charged, and therefore (ii) is attracted to the discharge electrode 3 so that the direction in which the composition in the mist form flows is determined.

The composition to be sprayed by use of the electrostatic spray device is stored in a storage reservoir 8, and is supplied to the spray electrode 1 via a pump (not illustrated) and a pipe (not illustrated). Further, the storage reservoir 8 is connected to the outside via a small hole air inlet 9 so that an inside of the storage reservoir 8 would not be negative-pressured while the composition is supplied to the spray electrode 1.

Furthermore, in a case where the spraying of the composition is repeated by use of the electrostatic spray device, the composition stored in the storage reservoir 8 is consumed. In this case, in order to continue using the electrostatic spray device, one of the following first and second arrangements can be employed.

The first arrangement is such that the electrostatic spray device can have an arrangement in which the composition can be added to the same storage reservoir 8. In this case, the storage reservoir 8 is detachable from the electrostatic spray device. The composition is added to the storage reservoir 8 after the storage reservoir 8 is detached from the electrostatic spray device. Then, the storage reservoir 8 to which the composition has been provided is attached to the electrostatic spray device again. Alternatively, the storage reservoir 8 can be fixed to the electrostatic spray device, and the storage reservoir 8 can have an opening via which the composition can be added into the storage reservoir 8.

The second arrangement is such that the storage reservoir 8 is attached to the electrostatic spray device so as to be exchangeable with another storage reservoir 8. The composition is supplied to the electrostatic spray device in such a manner that the storage reservoir 8 is replaced with another storage reservoir 8 in which the composition is stored. For example, the electrostatic spray device can be arranged such that a storage reservoir in which the composition is stored is provided as a cartridge spare part, and the cartridge spare part can be replaced with another cartridge spare part, if necessary. In this case, a specific arrangement of the cartridge spare part may be the one described in Japanese Translation of PCT international Publication, Tokuhyo, No. 2008-508150, for example.

As a matter of course, it is possible to arrange the electrostatic spray device such that the electrostatic spray device cannot be used anymore once all the composition stored in the storage reservoir 8 is consumed (that is, the electrostatic spray device has a disposable arrangement).

According to the electrostatic spray device, first, the composition is supplied, from the storage reservoir 8, to the spray electrode 1 having a tube shape, and a high voltage is applied to the composition in the spray electrode 1. Since the composition has an electric resistance in a predetermined range, as described above, the composition is charged and sprayed from an end of the spray electrode 1 by electrostatic force. The composition sprayed from the spray electrode 1 is electrically-charged with a voltage applied to the spray electrode 1. Accordingly, the composition thus sprayed is subjected to Coulomb repulsion so as to be sprayed in the atmosphere as being divided into fine particles. Here, the composition has, as described above, (i) a viscosity in a predetermined range, and (ii) a surface tension in a predetermined range. The composition can be therefore sprayed successfully, and can be divided into fine particles successfully.

In a case where a voltage is applied to the electrostatic spray device from the driving circuit 10 by, for example, insertion of an electric battery or an operation of a built-in electronic timer, the liquid stored in the storage reservoir 8 is sprayed from the spray electrode 1 in a form of fine particles so that the liquid is instantly vaporized in accordance with its vapor pressure and an ambient condition in the vicinity of the electronic spray device. An amount of the liquid thus sprayed can be determined in accordance with an amount of the ester compound, which amount is effective in controlling a harmful arthropod.

The electrostatic spray device can be arranged to supply the composition of the present invention either intermittently (e.g., at a predetermined load cycle) or continuously. A rate at which the composition is supplied may be, for example, a maximum amount of 5 g per day or a maximum amount of 3 g per day. Note, however, that the rate at which the composition is supplied is not limited to these.

With such an electrostatic spray device, a low-volatile constituent of the composition may accumulate on the spray electrode or in the vicinity of the spray electrode. This is a general problem of an electrostatic spray device. In a case where the accumulation of such a constituent occurs, the spray electrode may be partially clogged with or completely blocked with the composition. In this case, there is a risk that the electrostatic spraying cannot be carried out efficiently, or cannot be carried out at all. The risk is particularly high in a case where the spray electrode has a shape of a narrow tube.

In view of this, the composition of the present embodiment was used as the liquid to be sprayed by use of the electrostatic spray device, and was sprayed on such a spraying condition that (i) the ester compound in the composition had a relatively high concentration (e.g., 1.2% by mass of the ester compound) and (ii) the spraying was carried out for 14 days at such a load cycle that the composition was sprayed for 25 seconds every 2 minute. As a result, the spraying was stably carried out with substantially no accumulation of the composition on or in the vicinity of the spray electrode.

The composition subjected to the electrostatic spraying is observed as particles in the mist form. Accordingly, it is possible to determine qualitatively actual presence/absence of the composition thus sprayed, by visually checking the spray electrode (specifically, the spray electrode 1 illustrated in FIG. 1) and an area in the vicinity of the spray electrode.

Quantitative analysis with respect to the composition electrostatically sprayed can be carried out in such a manner that (i) the particles in the mist form are collected in the vicinity of the electrostatic spray device, and (ii) a quantity of the ester compound is determined in accordance with a method suitable for a sort of the ester compound thus used (e.g., High Performance Liquid Chromatography (HPLC) or a spectrophotometric method).

Further, the quantitative analysis can be also carried out by monitoring a change in mass of the entire electrostatic spray device or a change in mass of the storage reservoir (specifically, the storage reservoir 8 illustrated in FIG. 1).

An effect of a control process carried out by use of such an electrostatic spray device can be analyzed via a series of means that have been known by a person skilled in the art. For example, it is possible to analyze quantitatively a time period which is necessary to knock down (KD50) or kill (KT50) 50% of a parent population of harmful insects in a test chamber having a known size (e.g., a Peet-Grady chamber).

With such an arrangement, it becomes possible to spray electrostatically the composition to a harmful arthropod or an area where the harmful arthropod inhabits successfully, which composition is in a solid form at room temperature. Accordingly, the following effects can be achieved.

That is, according to the control method of the present embodiment, by electrostatically spraying a composition containing at least one of ester compounds represented by the respective formulas (1) through (5), it is possible to start and/or stop spraying the composition instantly, without carrying out any heating process (e.g., a smoking process) or any pressure process (e.g., a gas-pressure process or a mechanical pressure process). It becomes therefore easy to adjust an amount of the ester compound thus sprayed, and therefore becomes possible to suppress consumption of the ester compound. According to the control method of the present embodiment, it is therefore possible to carry out a process of controlling a harmful arthropod effectively.

Furthermore, according to the control method of the present embodiment, the composition containing at least one of the ester compound represented by the respective formulas (1) through (5) has (i) an electric resistance in a predetermined range, (ii) a viscosity in a predetermined range, and (iii) a surface tension in a predetermined range. That is, the composition has physical properties that are suitable for the electrostatic spraying. Accordingly, it is possible to spray the composition successfully, and control a harmful arthropod successfully.

Moreover, according to the control method of the present embodiment, by using a device that is suitable for the electrostatic spraying, it is possible to spray the composition successfully.

Further, according to the composition of the present embodiment, a composition (i) contains at least one of ester compounds represented by the respective formulas (1) through (5), which at least one of ester compounds is in a solid form at a standard atmospheric pressure, and (ii) has (a) an electric resistance in a predetermined range, (b) a viscosity in a predetermined arrange, and (c) a surface tension in a predetermined range. Accordingly, it becomes possible to control a wide variety of sorts of harmful arthropod, and provide the composition that is suitable for the electrostatic spraying.

Furthermore, according to the electrostatic spray device of the present embodiment, it is possible to spray composition easily without carrying out any heating process (e.g., a smoking process) or any pressure process (e.g., a gas-pressure process or a mechanical pressure process). Accordingly, with the electrostatic spray device of the present embodiment, it is possible to adjust an amount of the composition to be sprayed easily. It is therefore possible to suppress consumption of the ester compound which is an active constituent, and carry out a process for controlling a harmful arthropod effectively.

The present invention can be also arranged as described below.

The control method of the present invention is preferably arranged such that the composition has (i) an electric resistance of not less than $1\times10^3$ Ωm but not more than $1\times10^6$ Ωm at a temperature of 20° C., (ii) a viscosity of not less than 1 mPa·s but not more than 10 mPa·s at a temperature of 20° C., and (iii) a surface tension of not less than 20 mN/m but not more than 40 mN/m at a temperature of 20° C.

The control method of the present invention is preferably arranged such that the composition further contains a dispersion medium which contains (i) at least one compound selected from the group consisting of a polyol having at least one hydroxy group per molecule, a polyolether having at least one hydroxy group per molecule, 1-methoxy-2-propanol acetic ester, 1-buthoxy-2-propanol, 1-propoxy-2-acetoxypropane, and oxybis(methoxy) propane, and (ii) a physical property adjustment component, an amount of the at least one of ester compounds in the composition is not less than 0.1% by mass but not more than 10% by mass with respect to a total amount of the composition, an amount of the dispersion medium in the composition is not less than 90% by mass but not more than 99.9% by mass with respect to the total amount of the composition, and an amount of the physical property adjustment component in the composition is not less than 0.5% by mass but not more than 25% by mass with respect to the total amount of the composition.

The control method of the present invention is preferably arranged such that the composition further contains a dispersion medium for dispersing the at least one of ester compounds, and has a vapor pressure of less than 14 Pa at a temperature of 20° C., the dispersion medium containing (i) a low-vapor pressure component containing at least one compound selected from the group consisting of (I) a polyolether represented by the following general formula (6) and (II) a dibasic ester, and (ii) a resistivity adjustment component:

$$R^1O—[CH_2CH(CH_3)O]_n—H \quad (6)$$

(wherein: $R^1$ is a $C_1$ to $C_4$ alkyl group; and n is 2 or 3 (in a case where n is 2, $R^1$ is not a methyl group))

The control method of the present invention is preferably arranged such that the low-vapor pressure component further contains dipropylene glycol.

The control method of the present invention is preferably arranged such that the dispersion medium further contains a surface tension adjustment component.

The control method of the present invention is preferably arranged such that the low-vapor pressure component contains at least one compound selected from the group consisting of tripropylene glycol monomethyl ether, dipropylene glycol-n-propyl ether, dipropylene glycol-n-butyl ether, and a dibasic ester.

The control method of the present invention is preferably arranged such that the low-vapor pressure component contains dipropylene glycol-n-propyl ether.

The control method of the present invention is preferably arranged such that the dispersion medium contains (i) the low-vapor pressure component in an amount of not less than 75% by mass but not more than 98.9% by mass with respect to a total amount of the composition, (ii) the resistivity adjustment component in an amount of not less than 0.5% by mass but not more than 5% by mass with respect to the total amount of the composition, and (iii) the surface tension adjustment component in an amount of not less than 0.5% by mass but not more than 10% by mass with respect to the total amount of the composition.

The control method of the present invention is preferably arranged such that the dispersion medium contains (i), as the low-vapor pressure component, the compound represented by the general formula (6) in an amount of not less than 10% by mass but not more than 98.9% by mass with respect to the total amount of the composition, (ii), as the resistivity adjustment component, a 0.4% by mass sodium acetate solution in an amount of not less than 0.5% by mass but not more than 5% by mass with respect to the total amount of the composition, (iii), as the surface tension adjustment component, isoparaffin in an amount of not less than 0% by mass but not more than 9.99% by mass with respect to the total amount of the composition.

The control method of the present invention is preferably arranged such that the dispersion medium contains (i), as the low-vapor pressure component, in an amount of not less than 75% by mass but not more than 99.4% by mass with respect to the total amount of the composition, at least one compound selected from the group consisting of tripropylene glycol monomethyl ether, dipropylene glycol-n-propyl ether, dipropylene glycol-n-butyl ether, and a dibasic ester, (ii), as the resistivity adjustment component, (a) sodium acetate in an amount of not less than 0.0005% by mass but not more than 0.1% by mass with respect to the total amount of the composition, and (b) water in an amount of not less than 0.49% by mass but not more than 4.995% by mass with respect to the total amount of the composition, and (iii), as the surface tension adjustment component, isoparaffin in an amount of not less than 0% by mass but not more than 9.99% by mass with respect to the total amount of the composition.

The control method of the present invention is preferably arranged such that the dispersion medium contains, as the low-vapor pressure component, (i) dipropylene glycol-n-propyl ether in an amount of not less than 10% by mass but not more than 89.4% by mass with respect to the total amount of the composition, and (ii) the dibasic ester in an amount of not less than 10% by mass but not more than 89.4% by mass with respect to the total amount of the composition.

The control method of the present invention is preferably arranged such that the dispersion medium contains, as the low-vapor pressure component, the dibasic ester in an amount of not less than 10% by mass but not more than 45% by mass with respect to the total amount of the composition.

The control method of the present invention is preferably arranged such that the electrostatic spraying includes the steps of: supplying the composition into a spray electrode having a tube shape; applying a voltage across the spray electrode and a discharge electrode which corresponds to the spray electrode, so that the composition has a form of liquid particles; and spraying the composition from the spray electrode.

Note that, in the present specification, the term “liquid particles” means particles of a liquid, and a shape and a size of these liquid particles are not particularly limited. A shape of the liquid particles may be, but not limited to, a spherical shape. A size of the liquid particles is also not particularly limited. For example, in a case where the liquid particles have a spherical shape, such spherical liquid particles may have a diameter in a range of 1 nm to 1000 μm. Note, however, that the size of the spherical liquid particles is not limited to this.

The composition of the present invention preferably further includes a dispersion medium containing (i) at least one compound selected from the group consisting of a polyol having at least one hydroxy group per molecule, a polyolether having at least one hydroxy group per molecule, 1-methoxy-2-propanol acetic ester, 1-buthoxy-2-propanol, 1-propoxy-2-acetoxypropane, and oxybis(methoxy)propane, and (ii) a physical property adjustment component, an amount of the at least one of ester compounds in the composition being not less than 0.1% by mass but not more than 10% by mass with respect to a total amount of the composition, an amount of the dispersion medium in the composition being not less than 90% by mass but not more than 99.9% by mass with respect to the total amount of the composition, an amount of the physical property adjustment component in the composition being not less than 0.5% by mass but not more than 25% by mass with respect to a total amount of the composition.

The composition of the present invention preferably further includes: a dispersion medium for dispersing the ester compound, the dispersion medium containing (i) a low-vapor pressure component containing at least one compound selected from the group consisting of (a) a polyolether represented by the following general formula (6) and (b) a dibasic ester, and (ii) a resistivity adjustment component, the composition having a vapor pressure of less than 14 Pa at a temperature of 20° C.:

$$R^1O—[CH_2CH(CH_3)O]_n—H \quad (6)$$

(wherein: $R^1$ is a $C_1$ to $C_4$ alkyl group; and n is 2 or 3 (in a case where n is 2, $R^1$ is not a methyl group))

The composition of the present invention is preferably arranged such that the low-vapor pressure component further contains dipropylene glycol.

The composition of the present invention is preferably arranged such that the dispersion medium further contains a surface tension adjustment component.

The composition of the present invention is preferably arranged such that the low-vapor pressure component contains at least one compound selected from the group consisting of tripropylene glycol monomethyl ether, dipropylene glycol-n-propyl ether, dipropylene glycol-n-butyl ether, and a dibasic ester.

The composition of the present invention is preferably arranged such that the low-vapor pressure component contains dipropylene glycol-n-propyl ether.

The composition of the present invention is preferably arranged such that the dispersion medium contains (i) the low-vapor pressure component in an amount of not less than 75% by mass but not more than 98.9% by mass with respect to a total amount of the composition, (ii) the resistivity adjustment component in an amount of not less than 0.5% by mass but not more than 5% by mass with respect to the total amount of the composition, and (iii) the surface tension adjustment component in an amount of not less than 0.5% by mass but not more than 10% by mass with respect to the total amount of the composition.

The composition of the present invention is preferably arranged such that the dispersion medium contains (i), as the low-vapor pressure component, the compound represented by the general formula (6) in an amount of not less than 10% by mass but not more than 98.9% by mass with respect to the total amount of the composition, (ii), as the resistivity adjustment component, a 0.4% by mass sodium acetate solution in an amount of not less than 0.5% by mass but not more than 5% by mass with respect to the total amount of the composition, and (iii), as the surface tension adjustment component, isoparaffin in an amount of not less than 0% by mass but not more than 9.99% by mass with respect to the total amount of the composition.

The composition of the present invention is preferably arranged such that the dispersion medium contains (i), as the low-vapor pressure component, in an amount of not less than 75% by mass but not more than 99.4% by mass with respect to the total amount of the composition, at least one compound selected from the group consisting of tripropylene glycol monomethyl ether, dipropylene glycol-n-propyl ether, dipropylene glycol-n-butyl ether, and a dibasic ester, (ii), as the resistivity adjustment component, (a) sodium acetate in an amount of not less than 0.0005% by mass but not more than 0.1% by mass with respect to the total amount of the composition, and (b) water in an amount of not less than 0.49% by mass but not more than 4.995% by mass with respect to the total amount of the composition, and (iii), as the surface tension adjustment component, isoparaffin in an amount of not less than 0% by mass but not more than 9.99% by mass with respect to the total amount of the composition.

The composition of the present invention is preferably arranged such that the dispersion medium contains, as the low-vapor pressure component, (i) dipropylene glycol-n-propyl ether in an amount of not less than 10% by mass but not more than 89.4% by mass with respect to the total amount of the composition, and (ii) the dibasic ester in an amount of not less than 10% by mass but not more than 89.4% by mass with respect to the total amount of the composition.

The composition of the present invention is preferably arranged such that the dispersion medium contains, as the low-vapor pressure component, the dibasic ester in an amount of not less than 10% by mass but not more than 45% by mass with respect to the total amount of the composition.

An electrostatic spray device of the present invention includes: a storage reservoir for storing a composition of the present invention; a spray electrode to which the composition is supplied from the storage reservoir; and a discharge electrode provided in the vicinity of the spray electrode, the composition being electrostatically sprayed from the spray electrode by application of a voltage across the spray electrode and the discharge electrode.

Preferable embodiments of the present invention are thus explained above with reference to drawings. Note, however, that the present invention is not limited to the description of the embodiments above, but may be altered by a skilled person within the scope of the claims. The shapes of the constituents or combinations of the constituents, described in the above embodiments, are merely examples, and can be modified variously in accordance with design conditions or the like, within the technical scope of the present invention.

EXAMPLES

The present invention is explained below more specifically with Examples. Note, however, that the present invention is not limited to the following Examples.

In the following Examples, knock-down rates of flying insects (*Culex pipiens pallens*) in a test chamber (0.7 m×0.7 m×0.7 m) were found, and were compared with each other. In the following Examples, 20 female adult *Culex pipiens pallens* were released in the test chamber, which had been subjected to a control process in accordance with each of the following methods, and the number of *Culex pipiens pallens* that were knocked down was counted 10 minutes after the releasing. The knock-down rate was thus found.

Example 1

A composition of Example 1 was prepared as shown in the following Table 9.

TABLE 9

| | Content (percent by mass) |
|---|---|
| Ester compound represented by formula (1) | 0.5 |
| DPnP (Dipropylene glycol-n-propyl ether) | 87.5 |
| Isoparaffin (Isopar L (registered trademark)) | 8 |
| PEG300 (polyethylene glycol 300) | 2 |
| Water | 1.992 |
| Sodium acetate | 0.008 |
| Total | 100 |

(1)

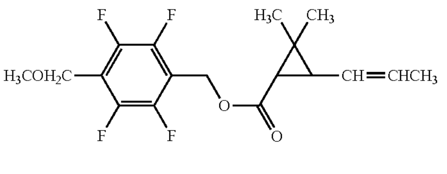

In the present Example, the ester compound represented by the formula (1) was [(2,3,5,6-tetrafluoro-4-(methoxymethyl) phenyl)]methyl=(1R)-trans-2,2-dimethyl-3-((Z)-1-propenyl)cyclopropane carboxylate.

The composition shown in the above Table 9 was supplied into a storage reservoir of an electrostatic spray device (Cleanaer model, manufactured by Atrium Innovation Ltd.) which had been disclosed in European Patent Application Publication No. 1399265. The electrostatic spray device was placed in the test chamber, and was turned on. The composition was continuously sprayed from the electrostatic spray device for initial 3 minutes immediately after the electrostatic spray device was turned on. Then the spraying was stopped for 1 minute. After that, the electrostatic spray device was started to operate again so that the spraying was carried out for 25 seconds every 2 minutes. As a result, a total of 25 mg of the composition was sprayed in the chamber. Then, an operation of the electrostatic spray device was stopped. An inside of the test chamber was thus subjected to a control process.

After that, 20 female adult *Culex pipiens pallens* were released in the test chamber. The number of *Culex pipiens pallens* that were knocked down was counted 30 minutes after they were released in the test chamber. A knock-down rate was thus found.

Example 2

A knock-down rate was found in the same manner as Example 1, except that a composition shown in the following Table 10 was employed in place of the composition shown in Table 9.

TABLE 10

| | Content (percent by mass) |
|---|---|
| Ester compound represented by formula (1) | 6 |
| DPnP (Dipropylene glycol-n-propyl ether) | 82 |
| Isoparaffin (Isopar L (registered trademark)) | 8 |
| PEG300 (polyethylene glycol 300) | 2 |
| Water | 1.992 |
| Sodium acetate | 0.008 |
| Total | 100 |

The following Table 11 shows results of Examples 1 and 2.

TABLE 11

| Sample | Knock-down rate of insects (%, 30 minutes after releasing) |
|---|---|
| Example 1 | 100 |
| Example 2 | 100 |

On the basis of the results of the measurement, it was shown that it was possible to control harmful arthropods highly efficiently with either (i) the composition and method of Example 1 or (ii) the composition and method of Example 2. Accordingly, usefulness of the present invention was confirmed.

Example 3

A composition of Example 3 was prepared as shown in the following Table 12.

TABLE 12

| | Content (percent by mass) |
|---|---|
| Ester compound represented by formula (2) | 1.2 |
| DPnP (Dipropylene glycol-n-propyl ether) | 84.5 |
| Isoparaffin (Isopar L (registered trademark)) | 8 |
| PEG300 (polyethylene glycol 300) | 4.8 |
| Water | 1.494 |
| Sodium acetate | 0.006 |
| Total | 100 |

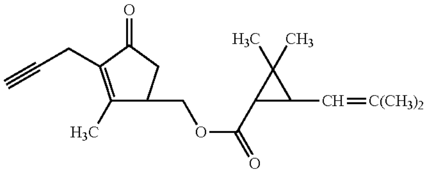

(2)

In the present Example, the ester compound represented by the formula (2) was (S)-2-methyl-4-oxo-3-(2-propynyl)-2-cyclopentenyl=(1R)-cis/trans-2,2-dimethyl-3-(2-methyl-1-propenyl)cyclopropane carboxylate.

The composition shown in the above Table 12 was supplied into a storage reservoir of an electrostatic spray device (Cleanaer model, manufactured by Atrium Innovation Ltd.), which had been disclosed in European Patent Application Publication No. 1399265. The electrostatic spray device was placed in a test chamber, and was turned on. The composition was continuously sprayed from the electrostatic spray device for initial 3 minutes immediately after the electrostatic spray device was turned on. Then, the spraying was stopped for 1 minute. After that, the electrostatic spray device was started to operate again so that the spraying was carried out for 25 seconds every 2 minutes. As a result, a total of 25 mg of the composition was sprayed in the chamber. Then, an operation of the electrostatic spray device was stopped. An inside of the test chamber was thus subjected to a control process.

After that, 20 female adult *Culex pipiens pallens* were released in the test chamber. The number of *Culex pipiens pallens* that were knocked down was counted 30 minutes after they were released in the test chamber. A knock-down rate was thus found.

Example 4

A knock-down rate was found in the same manner as Example 3, except that a composition shown in the following Table 13 was employed in place of the composition shown in Table 12.

TABLE 13

| | Content (percent by mass) |
|---|---|
| Ester compound represented by formula (2) | 6 |
| DPnP (Dipropylene glycol-n-propyl ether) | 84.5 |
| Isoparaffin (Isopar L (registered trademark)) | 8 |
| Water | 1.494 |
| Sodium acetate | 0.006 |
| Total | 100 |

The following Table 14 shows results of Examples 3 and 4.

TABLE 14

| Sample | Knock-down rate of insects (%, 30 minutes after releasing) |
|---|---|
| Example 3 | 100 |
| Example 4 | 100 |

On the basis of the results of the measurement, it was shown that it was possible to control harmful arthropods highly efficiently with either (i) the composition and method of Example 3 or (ii) the composition and method of Example 4. Accordingly, usefulness of the present invention was confirmed.

Example 5

A composition of Example 5 was prepared as shown in the following Table 15.

TABLE 15

| | Content (percent by mass) |
|---|---|
| Ester compound represented by formula (3) | 0.5 |
| DPnP (Dipropylene glycol-n-propyl ether) | 87.5 |
| Isoparaffin (Isopar L (registered trademark)) | 8 |
| PEG300 (polyethylene glycol 300) | 2 |
| Water | 1.992 |
| Sodium acetate | 0.008 |
| Total | 100 |

(3)

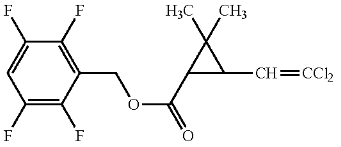

In the present Example, the ester compound represented by the formula (3) was (2,3,5,6-tetrafluoro phenyl)methyl=(1R)-trans-3-(2,2-dichlorovinyl)-2,2-dimethyl-cyclopropane carboxylate.

The composition shown in Table 15 was supplied into a storage reservoir of an electrostatic spray device (Cleanaer model, manufactured by Atrium Innovation Ltd.), which had been disclosed in European Patent Application Publication No. 1399265. The electrostatic spray device was placed in a test chamber, and was turned on. The composition was continuously sprayed from the electrostatic spray device for initial 3 minutes immediately after the electrostatic spray device was turned on. Then, the spraying was stopped for 1 minute. After that, the electrostatic spray device was started to operate again so that the spraying was carried out for 25 seconds every 2 minutes. As a result, a total of 25 mg of the composition was sprayed in the test chamber. Then, an operation of the electrostatic spray device was slopped. An inside of the test chamber was thus subjected to a control process.

After that, 20 female adult *Culex pipiens pallens* were released in the test chamber. The number of *Culex pipiens pallens* that were knocked down was counted 30 minutes after they were released in the test chamber. A knock-down rate was thus found.

Example 6

A knock-down rate was found in the same manner as Example 5, except that a composition shown in the following Table 16 was employed in place of the composition shown in Table 15.

TABLE 16

| | Content (percent by mass) |
|---|---|
| Ester compound represented by formula (3) | 6 |
| DPnP (Dipropylene glycol-n-propyl ether) | 82 |
| Isoparaffin (Isopar L (registered trademark)) | 8 |
| PEG300 (polyethylene glycol 300) | 2 |
| Water | 1.992 |
| Sodium acetate | 0.008 |
| Total | 100 |

The following Table 17 shows results of Examples 5 and 6.

TABLE 17

| Sample | Knock-down rate of insects (%, 30 minutes after releasing) |
|---|---|
| Example 5 | 100 |
| Example 6 | 100 |

On the basis of results of the measurement, it was shown that it was possible to control harmful arthropods highly efficiently with either (i) the composition and method of Example 5 or (ii) the composition and method of Example 6. Accordingly, usefulness of the present invention was confirmed.

Example 7

A composition of Example 7 was prepared as shown in Table 18.

TABLE 18

| | Content (percent by mass) |
|---|---|
| Ester compound represented by formula (4) | 1.2 |
| DPnP (Dipropylene glycol-n-propyl ether) | 84.5 |
| Isoparaffin (Isopar L (registered trademark)) | 8 |
| PEG300 (polyethylene glycol 300) | 4.8 |
| Water | 1.494 |
| Sodium acetate | 0.006 |
| Total | 100 |

(4)

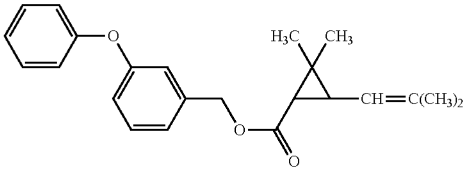

In the present Example, the ester compound represented by the formula (4) was 3-phenoxybenzyl=(1R)-cis/trans-2,2-dimethyl-3-(2-methyl-1-propenyl)cyclopropane carboxylate.

The composition shown in the above Table 18 was supplied into a storage reservoir of an electrostatic spray device (Cleanaer model, manufactured by Atrium Innovation Ltd.), which had been disclosed in European Patent Application Publication No. 1399265. The electrostatic spray device was placed in a test chamber, and was turned on. The composition was continuously sprayed from the electrostatic spray device for initial 3 minutes immediately after the electrostatic spray device was turned on. Then, the spraying was stopped for 1 minute. After that, the electrostatic spray device was started to operate again so that the spraying was carried out for 25 seconds every 2 minutes. As a result, a total of 25 mg of the composition was sprayed in the test chamber. Then, an operation of the electrostatic spray device was stopped. An inside of the test chamber was thus subjected to a control process.

After that, 20 female adult *Culex pipiens pallens* were released in the test chamber. The number of *Culex pipiens pallens* that were knocked down was counted 30 minutes after they were released in the test chamber. A knock-down rate was thus found.

Example 8

A knock-down rate was found in the same manner as Example 7, except that a composition shown in the following Table 19 was employed in place of the composition shown in Table 18.

TABLE 19

| | Content (percent by mass) |
|---|---|
| Ester compound represented by formula (4) | 6 |
| DPnP (Dipropylene glycol-n-propyl ether) | 84.5 |
| Isoparaffin (Isopar L (registered trademark)) | 8 |
| Water | 1.494 |
| Sodium acetate | 0.006 |
| Total | 100 |

The following Table 20 shows results of Examples 7 and 8.

TABLE 20

| Sample | Knock-down rate of insects (%, 30 minutes after releasing) |
|---|---|
| Example 7 | 100 |
| Example 8 | 100 |

On the basis of results of the measurement, it was shown that it was possible to control harmful arthropods highly efficiently with er (i) the composition and method of Example 7 or (ii) the composition and method of Example 8. Accordingly, usefulness of the present invention was confirmed.

Example 9

A composition of Example 9 was prepared as shown in the following Table 21.

TABLE 21

| | Content (percent by mass) |
|---|---|
| Ester compound represented by formula (5) | 1.2 |
| DPnP (Dipropylene glycol-n-propyl ether) | 84.5 |
| Isoparaffin (Isopar L (registered trademark)) | 8 |
| PEG300 (polyethylene glycol 300) | 4.8 |
| Water | 1.494 |
| Sodium acetate | 0.006 |
| Total | 100 |

(5)

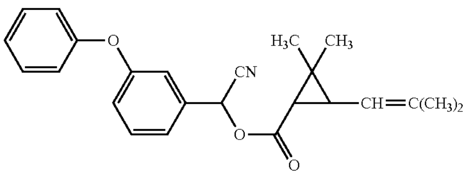

In the present Example, the ester compound represented by the formula (5) was (R,S)-α-cyano-3-phenoxybenzyl=(1R)-cis/trans-2,2-dimethyl-3-(2-methyl-1-propenyl)cyclopropane carboxylate.

The composition shown in the above Table 21 was supplied into a storage reservoir of an electrostatic spray device (Cleanaer model, manufactured by Atrium Innovation Ltd.), which had been disclosed in European Patent Application Publication No. 1399265. The electrostatic spray device was placed in a test chamber, and was turned on. The composition was continuously sprayed from the electrostatic spray device for initial 3 minutes immediately after the electrostatic spray device was turned on. Then, the spraying was stopped for 1 minute. After that, the electrostatic spray device was started to operate again so that the spraying was carried out for 25 seconds every 2 minutes. As a result, a total of 25 mg of the composition was sprayed in the test chamber. Then, an operation of the electrostatic spray device was stopped. An inside of the test chamber was thus subjected to a control process.

After that, 20 female adult *Culex pipiens pallens* were released in the test chamber. The number of *Culex pipiens pallens* that were knocked down was counted 30 minutes after they were released in the test chamber. A knock-down rate was thus found.

Example 10

A knock-down rate was found in the same manner as Example 9, except that a composition shown in Table 22 was employed in place of the composition shown in Table 21.

TABLE 22

| | Content (percent by mass) |
|---|---|
| Ester compound represented by formula (5) | 6 |
| DPnP (Dipropylene glycol-n-propyl ether) | 84.5 |

TABLE 22-continued

| | Content (percent by mass) |
|---|---|
| Isoparaffin (Isopar L (registered trademark)) | 8 |
| Water | 1.494 |
| Sodium acetate | 0.006 |
| Total | 100 |

The following Table 23 shows results of Examples 9 and 10.

TABLE 23

| Sample | Knock-down rate of insects (%, 30 minutes after releasing) |
|---|---|
| Example 9 | 100 |
| Example 10 | 100 |

On the basis of results of the measurement, it was shown that it was possible to control harmful arthropods highly efficiently with either (i) the composition and method of Example 9 or (ii) the composition and method of Example 10. Accordingly, usefulness of the present invention was confirmed.

Example 11

A knock-down rate was found in the same manner as Example 1, except that a composition shown in the following Table 24 was employed in place of the composition shown in Table 9.

TABLE 24

| | Content (percent by mass) |
|---|---|
| Ester compound represented by formula (1) | 10 |
| (2-methoxymethylethoxy) propanol (Dowanol DPM (registered trademark)) | Residue |
| Isoparaffin (Isopar L (registered trademark)) | 8 |
| Water | 1.4334 |
| Sodium acetate | 0.0066 |
| Total | 100 |

The following Table 25 shows a result of Example 11.

TABLE 25

| Sample | Knock-down rate of insects (%, 30 minutes after releasing) |
|---|---|
| Example 11 | 100 |

Example 12

In the present Example, a composition shown in Table 24 was employed.

In the present Example, an example of the present invention and a comparison example were compared with each other in knock-down rate of flying insects (*Culex pipiens pallens*) released in a test chamber (1.8 m×1.8 m×1.8 m). According to the present example, a knock-down rate was found in such a manner that (i) 50 female *Culex pipiens pallens* were released in a test chamber which had been subjected to a control process, and (ii) the number of *Culex pipiens pallens* that were knocked down was counted 2 minutes after they were released in the test chamber.

A composition shown in Table 24 was supplied into a storage reservoir of an electrostatic spray device (Cleanaer model, manufactured by Atrium Innovation Ltd.), which had been disclosed in European Patent Application Publication No. 1399265. The electrostatic spray device was placed in the test chamber, and was turned on. The composition was continuously sprayed from the electrostatic spray device for initial 3 minutes immediately after the electrostatic spray device was turned on. Then, the spraying was stopped for 1 minute. After that, the electrostatic spray device was started to operate again so that the spraying was carried out for 25 seconds every 2 minutes. As a result, a total of 25 mg of the composition was sprayed in the test chamber. Then, an operation of the electrostatic spray device was stopped. An inside of the test chamber was thus subjected to a control process.

After that, 50 female *Culex pipiens pallens* were released in the test chamber. The number of *Culex pipiens pallens* that were knocked down was counted 2 minutes after they were released in the test chamber. A knock-down rate was thus found.

Comparative Example

Into an aerosol can, 0.333 parts by mass of [(2,3,5,6-tetrafluoro-4-(methoxymethyl)phenyl)]methyl=(1R)-trans-2, 2-dimethyl-3-((Z)-1-propenyl)cyclopropane carboxylate, and 59.677 parts by mass of (2-methoxymethylethoxy)propanol (Dowanol DPM (registered trademark)) were provided. Then, a valve section was attached to the aerosol can, and 40 parts by mass of a propellant (compressed petroleum gas) was supplied into the aerosol can via the valve section. A total of 100 parts by mass of aerosol (hereinafter, referred to as “Comparative Example 1”) was thus obtained.

Into the test chamber, 750 mg of Comparative Example 1 was sprayed.

After that, 50 female *Culex pipiens pallens* were released in the test chamber. Then, the number of *Culex pipiens pallens* that were knocked down was counted 2 minutes after they were released in the test chamber. A knock-down rate was thus found.

The following Table 26 shows results of Example 12 and Comparative Example 1.

TABLE 26

| Sample | Knock-down rate of insects (%, 2 minutes after releasing) |
|---|---|
| Example 12 | 94 |
| Comparative Example 1 | 72 |

The measurement shows that Example 12 was higher in knock-down rate than Comparative Example 1. That is, with Example 12, it was possible to control *Culex pipiens pallens* highly efficiently. Usefulness of the present invention was thus confirmed.

INDUSTRIAL APPLICABILITY

Each of a control method, a composition, and an electrostatic spray device of the present invention makes it possible to control a harmful arthropod effectively, without carrying out any heating process or any pressure process. The present invention is therefore applicable to a process of controlling a harmful arthropod indoors (such as a house and a factory) or outdoors (such as a farm and a park).

REFERENCE SIGNS LIST

1. Spray electrode
2. Depression for spray electrode
3. Discharge electrode
4. Depression for discharge electrode
5. Spray discharge surface
6. Sheathed metal pipe
7. Sheathed metal pipe
8. Storage reservoir
9. Small hole air inlet
10. Driving circuit

The invention claimed is:

1. An electrostatic spray device comprising:

a storage reservoir for storing a composition;

a spray electrode to which the composition is supplied from the storage reservoir; and a discharge electrode provided in the vicinity of the spray electrode, the composition being electrostatically sprayed from the spray electrode by application of a voltage across the spray electrode and the discharge electrode, the composition comprising at least one of ester compounds represented by the following formulas (1) through (5), respectively:

(1)

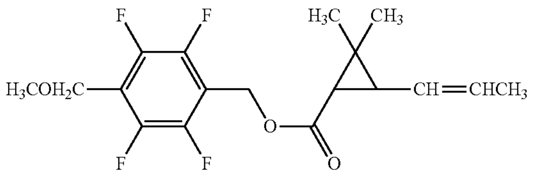

(2)

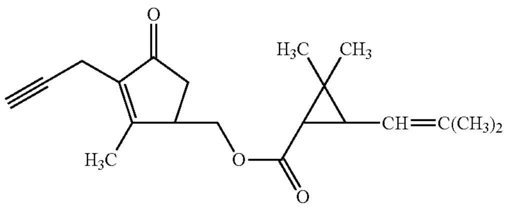

(3)

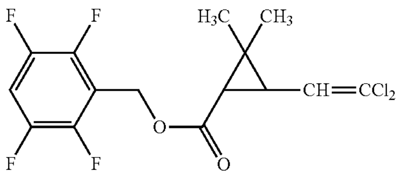

-continued (4)

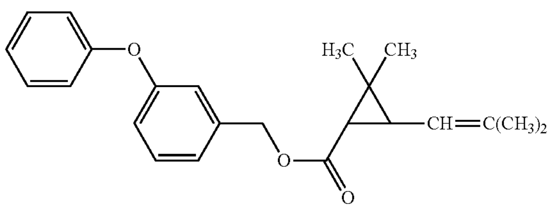

(5)

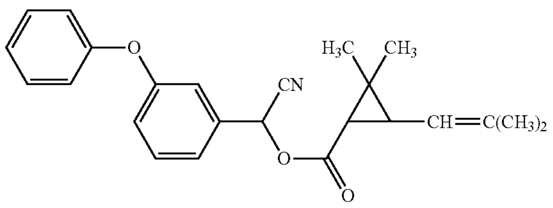

wherein the composition has (i) an electric resistance of not less than $1\times10^3$ Ωm but not more than $1\times10^6$ Ωm at a temperature of 20° C., (ii) a viscosity of not less than 1 mPa·s but not more than 10 mPa·s at a temperature of 20° C., and (iii) a surface tension of not less than 20 mN/m but not more than 40 mN/m at a temperature of 20° C.;

the composition further containing a dispersion medium for dispersing the at least one of ester compounds, and having a vapor pressure of less than 14 Pa at a temperature of 20° C.;

the dispersion medium containing (i) a low-vapor pressure component containing dipropylene glycol-n-propyl ether, (ii) a resistivity adjustment component, and (iii) a surface tension adjustment component.

2. The electrostatic spray device as set forth in claim 1, wherein:

the dispersion medium contains (i) dipropylene glycol-n-propyl ether, and (ii) a physical property adjustment component;

an amount of the at least one of ester compounds in the composition is not less than 0.1% by mass but not more than 10% by mass with respect to a total amount of the composition;

an amount of the dispersion medium in the composition is not less than 90% by mass but not more than 99.9% by mass with respect to the total amount of the composition; and an amount of the physical property adjustment component in the composition is not less than 0.5% by mass but not more than 25% by mass with respect to the total amount of the composition.

* * * * *